(12) United States Patent
Mehta et al.

(10) Patent No.: US 8,882,753 B2
(45) Date of Patent: *Nov. 11, 2014

(54) DEVICES AND METHODS FOR PERCUTANEOUS ENERGY DELIVERY

(75) Inventors: Bankim H. Mehta, San Ramon, CA (US); Scott A. McGill, San Ramon, CA (US)

(73) Assignee: Syneron Medical Ltd, Yokneam Illit (IL)

( * ) Notice: Subject to any disclaimer, the term of this patent is extended or adjusted under 35 U.S.C. 154(b) by 1311 days.

This patent is subject to a terminal disclaimer.

(21) Appl. No.: 12/249,790

(22) Filed: Oct. 10, 2008

(65) Prior Publication Data

US 2010/0010480 A1    Jan. 14, 2010

Related U.S. Application Data

(60) Provisional application No. 61/080,386, filed on Jul. 14, 2008, provisional application No. 61/099,671, filed on Sep. 24, 2008.

(51) Int. Cl.

| A61B 18/20 | (2006.01) |
|---|---|
| A61B 18/22 | (2006.01) |
| A61B 18/18 | (2006.01) |
| A61B 18/14 | (2006.01) |
| A61N 5/067 | (2006.01) |
| A61B 18/12 | (2006.01) |
| A61B 18/00 | (2006.01) |
| A61N 7/02 | (2006.01) |

(52) U.S. Cl.
CPC .......... *A61B 18/203* (2013.01); *A61B 18/1206* (2013.01); *A61B 2018/00875* (2013.01); *A61B 2018/1425* (2013.01); *A61B 2018/00011* (2013.01); *A61B 2018/208* (2013.01); *A61B 2018/1807* (2013.01); *A61B 18/1477* (2013.01); *A61B 18/14* (2013.01); *A61B 2018/1475* (2013.01); *A61N 7/02* (2013.01); *A61B 2018/00452* (2013.01); *A61B 2018/143* (2013.01); *A61B 18/18* (2013.01); *A61B 2018/00994* (2013.01); *A61B 18/20* (2013.01)
USPC .......... 606/9; 606/16; 606/31; 606/32; 606/33; 607/89; 607/96; 607/99; 607/101; 607/102; 128/898

(58) Field of Classification Search
None
See application file for complete search history.

(56) References Cited

U.S. PATENT DOCUMENTS

| 1,935,605 | A | * | 11/1933 | Altruda .................... 606/132 |
|---|---|---|---|---|
| 4,250,617 | A | * | 2/1981 | Bakker et al. .................. 30/34.2 |
| 5,102,397 | A | | 4/1992 | Brunet |
| 5,697,281 | A | * | 12/1997 | Eggers et al. ................. 604/114 |
| 5,797,903 | A | | 8/1998 | Swanson et al. |
| 6,024,733 | A | * | 2/2000 | Eggers et al. ................. 604/500 |
| 6,059,820 | A | * | 5/2000 | Baronov ..................... 607/89 |
| 6,249,706 | B1 | | 6/2001 | Sobota et al. |
| 6,277,116 | B1 | * | 8/2001 | Utely et al. ..................... 606/42 |
| 6,293,925 | B1 | | 9/2001 | Safabash et al. |
| 6,306,152 | B1 | * | 10/2001 | Verdonk et al. .............. 606/182 |
| 6,425,912 | B1 | * | 7/2002 | Knowlton .................... 607/101 |
| 6,537,242 | B1 | * | 3/2003 | Palmer ......................... 604/22 |

(Continued)

*Primary Examiner* — Lynsey Crandall
*Assistant Examiner* — Manolis Pahakis
(74) *Attorney, Agent, or Firm* — Smith Risley Tempel Santos LLC; Gregory Scott Smith

(57) ABSTRACT

The invention provides a system and method for percutaneous energy delivery in an effective, manner using one or more probes. Additional variations of the system include array of probes configured to minimize the energy required to produce the desired effect.

17 Claims, 24 Drawing Sheets

(56) References Cited

U.S. PATENT DOCUMENTS

| | | | |
|---|---|---|---|
| 6,584,360 B2 | 6/2003 | Francischelli et al. | |
| 6,595,911 B2 | 7/2003 | LoVuolo | |
| 6,632,219 B1* | 10/2003 | Baranov et al. | 606/9 |
| 6,662,054 B2* | 12/2003 | Kreindel et al. | 607/101 |
| 6,743,211 B1* | 6/2004 | Prausnitz et al. | 604/239 |
| 6,752,817 B2* | 6/2004 | Flora et al. | 606/181 |
| 6,766,202 B2* | 7/2004 | Underwood et al. | 607/99 |
| 6,896,666 B2* | 5/2005 | Kochamba | 604/141 |
| 7,013,179 B2* | 3/2006 | Carter et al. | 607/69 |
| 7,087,035 B2* | 8/2006 | Trautman et al. | 604/22 |
| 7,278,991 B2* | 10/2007 | Morris et al. | 606/41 |
| 7,377,903 B2* | 5/2008 | Raney | 600/583 |
| 7,422,586 B2* | 9/2008 | Morris et al. | 606/41 |
| 7,494,488 B2 | 2/2009 | Weber | |
| 7,993,366 B2* | 8/2011 | Yassinzadeh et al. | 606/213 |
| 8,007,493 B2* | 8/2011 | McGill et al. | 606/32 |
| 8,133,216 B2* | 3/2012 | Knopp et al. | 606/32 |
| 8,142,426 B2* | 3/2012 | Knopp et al. | 606/31 |
| 8,273,080 B2* | 9/2012 | Mehta | 606/32 |
| 2001/0039415 A1 | 11/2001 | Francischelli et al. | |
| 2002/0032415 A1* | 3/2002 | Trautman et al. | 604/272 |
| 2002/0120260 A1* | 8/2002 | Morris et al. | 606/41 |
| 2002/0120261 A1 | 8/2002 | Morris et al. | |
| 2003/0032950 A1* | 2/2003 | Altshuler et al. | 606/9 |
| 2003/0083607 A1 | 5/2003 | Bobo | |
| 2003/0125604 A1 | 7/2003 | Kochamba et al. | |
| 2004/0127895 A1* | 7/2004 | Flock et al. | 606/41 |
| 2004/0181203 A1* | 9/2004 | Cormier et al. | 604/500 |
| 2005/0195726 A1 | 9/2005 | Bullington et al. | |
| 2005/0197666 A1* | 9/2005 | Raney | 606/181 |
| 2005/0222565 A1* | 10/2005 | Manstein | 606/41 |
| 2006/0047281 A1* | 3/2006 | Kreindel | 606/49 |
| 2006/0058712 A1* | 3/2006 | Altshuler et al. | 601/15 |
| 2006/0116669 A1* | 6/2006 | Dolleris | 606/17 |
| 2006/0264926 A1* | 11/2006 | Kochamba | 606/41 |
| 2007/0055179 A1* | 3/2007 | Deem et al. | 601/2 |
| 2007/0129714 A1* | 6/2007 | Elkins et al. | 606/21 |
| 2007/0142885 A1* | 6/2007 | Hantash et al. | 607/102 |
| 2007/0244368 A1 | 10/2007 | Bayloff et al. | |
| 2007/0255355 A1* | 11/2007 | Altshuler et al. | 607/86 |
| 2008/0071258 A1* | 3/2008 | Lemberg et al. | 606/33 |
| 2008/0091182 A1 | 4/2008 | Mehta | |
| 2008/0091183 A1* | 4/2008 | Knopp et al. | 606/31 |
| 2008/0091184 A1* | 4/2008 | Knopp et al. | 606/31 |
| 2008/0091185 A1* | 4/2008 | McGill et al. | 606/31 |
| 2008/0215039 A1* | 9/2008 | Slatkine et al. | 606/9 |
| 2008/0248554 A1* | 10/2008 | Merchant et al. | 435/259 |
| 2008/0281389 A1* | 11/2008 | Knopp et al. | 607/115 |
| 2009/0036958 A1 | 2/2009 | Mehta | |
| 2009/0054842 A1* | 2/2009 | Yeshurun et al. | 604/173 |
| 2009/0112205 A1 | 4/2009 | McGill et al. | |
| 2011/0144729 A1 | 6/2011 | Weber | |

\* cited by examiner

DEVICES AND METHODS FOR PERCUTANEOUS ENERGY DELIVERY

CROSS-REFERENCE

This application is a non-provisional of U.S. Provisional Application No. 61/080,386 filed Jul. 14, 2008 and a non-provisional of U.S. Provisional Application No. 61/099,671 filed Sep. 24, 2008.

BACKGROUND OF THE INVENTION

The systems and method discussed herein treat tissue in the human body. In a particular variation, systems and methods described below treat cosmetic conditions affecting, the skin of various body parts, including face, neck, and other areas traditionally prone to wrinkling, lines, sagging and other distortions of the skin.

Exposure of the skin to environmental forces can, over time, cause the skin to sag, wrinkle, form lines, or develop other undesirable distortions. Even normal contraction of facial and neck muscles, e.g. by frowning or squinting, can also over time form furrows or bands in the face and neck region. These and other effects of the normal aging process can present an aesthetically unpleasing cosmetic appearance.

Accordingly, there is well known demand for cosmetic procedures to reduce the visible effects of such skin distortions. There remains a large demand for "tightening" skin to remove sags and wrinkles especially in the regions of the face and neck.

One method surgically resurfaces facial skin by ablating the outer layer of the skin (from 200 µm to 600 µm), using laser or chemicals. In time, a new skin surface develops. The laser and chemicals used to resurface the skin also irritate or heat the collagen tissue present in the dermis. When irritated or heated in prescribed ways, the collagen tissue partially dissociates and, in doing so, shrinks. The shrinkage of collagen also leads to a desirable "tightened" look. Still, laser or chemical resurfacing leads to prolonged redness of the skin, infection risk, increased or decreased pigmentation, and scarring.

Lax et al. U.S. Pat. No. 5,458,596 describes the use of radio frequency energy to shrink collagen tissue. This cosmetically beneficial effect can be achieved in facial and neck areas of the body in a minimally intrusive manner, without requiring the surgical removal of the outer layers of skin and the attendant problems just listed.

Utely et al. U.S. Pat. No. 6,277,116 also teaches a system for shrinking collagen for cosmetically beneficial purposes by using an electrode array configuration.

However, areas of improvement remain with the previously known systems. In one example, fabrication of an electrode array may cause undesired cross-current paths forming between adjacent electrodes resulting in an increase in the amount of energy applied to tissue.

Thermage, Inc. of Hayward Calif. also holds patents and sells devices for systems for capacitive coupling of electrodes to deliver a controlled amount of radiofrequency energy. This controlled delivery of RF energy creates an electric field through the epidermis that generates "resistive heating" in the skin to produce cosmetic effects while simultaneously attempting to cool the epidermis with a second energy source to prevent external burning of the epidermis.

In such systems that treat in a non-invasive manner, generation of energy to produce a result at the dermis results in unwanted energy passing to the epidermis. Accordingly, excessive energy production creates the risk of unwanted collateral damage to the skin.

In view of the above, there remains a need for an improved energy delivery system. Such systems may be designed to create an improved electrode array delivery system for cosmetic treatment of tissue. In particular, such an electrode array may provide deep uniform heating by applying energy to tissue below the epidermis to cause deep structures in the skin to immediately tighten. There also remains a need to provide systems that can deliver energy to a predetermined target area while minimizing delivery of energy to undesired region of tissue.

Over time, new and remodeled collagen may further produce a tightening of the skin, resulting in a desirable visual appearance at the skin's surface. Such systems can also provide features that increase the likelihood that the energy treatment will be applied to the desired target region. Moreover, devices and systems having disposable or replaceable energy transfer elements provide systems that offer flexibility in delivering customized treatment based on the intended target tissue.

The systems of the present invention are also adapted to apply energy selectively to tissue to spare select tissue structures, to control creation of a lesion from a series of discrete lesions to a continuous lesion, and to selectively create fractional lesions to optimize effectiveness of the treatment.

Moreover, the features and principles used to improve these energy delivery systems can be applied to other areas, whether cosmetic applications outside of reduction of skin distortions or other medical applications.

SUMMARY OF THE INVENTION

The invention provides improved systems and methods of percutaneously delivering energy to tissue where the systems and methods enable a physician (or other medical practitioner) to precisely control the areas or region of tissue that receives energy. In one aspect of the invention, the methods and systems produce cosmetically beneficial effects of using energy to shrink collagen tissue in the dermis in an effective manner that prevents the energy from affecting the outer layer of skin. However, the devices and method described herein can target the underlying layer of adipose tissue or fat for lipolysis or the breakdown of fat cells. Selecting probes having sufficient length to reach the subcutaneous fat layer allows for such probes to apply energy in the subcutaneous fat layer. Application of the energy can break down the fat cells in that layer allowing the body to absorb the resulting free fatty acids into the blood stream. Such a process can allow for contouring of the body surface for improved appearance. Naturally, such an approach can be used in the reduction of cellulite. In addition, the systems and methods are also useful for treating other skin surface imperfections and blemishes by application of a percutaneous treatment.

The devices described herein generally include energy delivery devices for delivering energy from an energy supply unit to a target region beneath a surface of tissue. In one variation, the device includes a device body having a handle portion, and a tissue engaging surface, where the tissue engaging surface allows orientation of the device body on the surface of tissue; a first plurality of energy transfer elements being advanceable from the device body at an oblique angle relative to the tissue engaging surface; a stabilization plate adjacent to the tissue engaging surface and being spaced from the plurality of energy transfer elements; and a connector adapted to couple the energy supply unit to the plurality of energy transfer elements; wherein the tissue engaging surface and stabilization plate are positioned such that when the tissue engaging surface is placed on the surface of tissue and the first plurality of energy transfer elements is advanced into the surface of tissue at an entry point, the first plurality of energy transfer elements enters the tissue at the oblique angle relative to the tissue surface while the tissue engaging surface and the stabilization plate reduce movement of the surface of tissue adjacent to the entry point.

The device may also include a window located between the stabilization plate and the tissue engaging surface, where die window is configured to permit direct visualization of advancement of the energy transfer elements into the entry point. In some variations, the window is sized to outline a perimeter of the energy delivery region created by the energy transfer elements. In additional variations, the window is sized to outline a distal length of the energy transfer elements when extended. Alternatively, the entire stabilization plate can be sized to outline a perimeter of the energy delivery region created by the energy transfer elements or to outline a distal length of the energy transfer elements when extended.

The window can comprise an opening in the stabilization plate or the window can comprise a transparent material having an outline or mark to denote the perimeter of the window.

The stabilization plate can also include a cooling source coupled thereto, such that the stabilization plate maintains a temperature at, below, or slightly above body temperature. In some variation, the cooling source can include one or more heat pipes that permit placement of at least a portion of the cooling source towards a proximal end of the device body. This permits spacing of the cooling source from the stabilization plate to prevent visual interference of the stabilization plate.

The cooling source can comprise any number of cooling modes. For example, the cooling modes can be selected from a thermo electric cooler, a fan, a cooling fluid, a phase-change type material that absorbs heat during the phase change or a combination thereof. Such phase change materials include materials that are designed for melting and solidifying at a certain temperature, and are capable of storing and releasing large amounts of energy. Heat is absorbed or released when the material changes from solid to liquid and vice versa. For example: Ice, Salt Hydrates and Eutectic Salts, ($MnH2O$).

In addition, the stabilization plate can include any number of features to assist in monitoring temperature or treatment. For example, a surface of the stabilization plate can be configured to change color in response to a rise in temperature. Moreover, the stabilization plate can include one or more suction lumens to assist in contacting tissue. A surface of the stabilization plate can include any number of friction increasing features. For example, the surface can include projections, barbs, or a roughened surface.

The energy delivery devices can further include cartridges that are removably coupled to the device body, where at least the plurality of first electrodes and the tissue engaging surface are located on or in the cartridge body. In some variations, the cartridge and/or energy delivery elements can be coupled to an actuator, where movement of the actuator causes advancement or retraction of the first plurality of electrodes.

The invention further includes methods for applying energy to a region of tissue from a energy source, comprising: placing a tissue engaging surface of an energy delivery device against a surface of the tissue; placing a stabilization plate of the energy delivery device adjacent to the tissue engaging surface; advancing a plurality of energy transfer elements from a retracted position within the energy delivery device into a treatment position in a region of tissue between the tissue engaging surface and the stabilization plate, where the energy transfer elements extend from the treatment device at an oblique angle relative to the tissue engaging surface; and applying energy to tissue at an active region of at least one of the plurality of energy transfer elements.

In one variation of the method, the plurality of energy transfer elements are comprised of a plurality of electrodes and where applying energy to tissue at an active region of at least one of the plurality of electrodes comprises first measuring an impedance of each electrode; and applying energy to those electrodes measuring impedance between a range of pre-determined impedance values. For example, when treating a dermis region of tissue, the range of pre-determined impedance values comprises between 700Ω to 3000Ω.

In another variation, the invention includes a system for applying energy to a target layer of tissue within a plurality of tissue layers, the system comprising: at least one probe having an active area coupled to a device body, the probe being configured to measure a tissue parameter adjacent to the active area; a power supply coupled to the probe, the power supply having a controller to adjust energy delivery to the probe in response to the parameter.

In one variation of the system, there are a plurality of probes each having an active area and each probe being configured measure the tissue parameter adjacent to the respective active area. In another variation, the probes include a first sensor located on the active area. In addition, the probes can include a second sensor located on a non-active area of the probe.

In certain variations, the controller of the system can prevents energy delivery to the probe when the tissue parameter is less than 250 ohms or greater than 3000 ohms. When the impedance is between 700 and 1500 ohms the controller can provide energy at a first set of parameters, and when the tissue parameter is between 1500 and 3000 ohms the controller can provide energy at a second set of parameters to account for the varying tissue.

In an additional variation, the invention includes systems and methods treating tissue, such systems and methods comprising an array of electrode pairs adapted to penetrate the tissue. a controller for providing energy to the array of electrode pairs, where the controller independently controls application of energy between electrode pairs in the array to limit flow of energy to between each electrode in the pair to create a plurality of fractional lesions within the tissue between adjacent electrode pairs.

It is expressly intended that, wherever possible, the invention includes combinations of aspects of the various embodiments described herein or even combinations of the embodiments themselves.

In addition, the concepts disclosed herein can be combined with the following commonly assigned applications where such combinations are possible: U.S. patent application Ser. No. 11/676,230 entitled "METHODS AND DEVICES FOR TREATING TISSUE filed on Feb. 16, 2007; PCT application No.: PCT/US2007/081556 entitled "METHODS AND DEVICES FOR TREATING TISSUE filed on Oct. 16, 2007; U.S. patent application Ser. No. 11/764,032 entitled "METHODS AND DEVICES FOR TREATING TISSUE filed on Jun. 15, 2007; and U.S. patent application Ser. No. 11/832,544 entitled "METHODS AND DEVICES FOR TREATING TISSUE filed on Aug. 1, 2007. Each of which is incorporated by reference herein.

DESCRIPTION OF THE PREFERRED EMBODIMENT

The systems and method discussed herein treat tissue in the human body. In one variation, the systems and methods treat cosmetic conditions affecting the skin of various body parts, including face, neck, and other areas traditionally prone to wrinkling, lines, sagging and other distortions of the skin. The methods and systems described herein may also have application in other surgical fields apart from cosmetic applications.

The inventive device and methods also include treatment of skin anomalies such as warts (*Verruca plana, Verruca vulgaris*), sebaceous hyperplasia or acne (*Acne vulgaris*). Treatment of acne can be accomplished by the direct ablation of sebaceous glands or it can be accomplished by the delivery of thermal energy which will stimulate the body's immune system to eliminate the bacteria, Propionibacterium acnes, which is one of the causes of acne. The methods and devices can be used for the removal of unwanted hair (i.e., depilation) by applying energy or heat to permanently damage hair follicles thereby removing the skins ability to grow hair. Such treatment may be applied on areas of facial skin as well as other areas of the body.

Other possible uses include pain management (both in the use of heat to reduce pain in muscle tissue and by directly ablating nociceptive pain fibers), stimulation of cellular healing cascade via heat, treatment of the superficial muscular aponeurotic system (SMAS), reproductive control by elevated heating of the testicles, and body modification such as piercing, scarification or tattoo removal In addition to therapeutic surface treatments of the skin, the current invention can be targeted to the underlying layer of adipose tissue or fat for lipolysis or the breakdown of fat cells. Selecting probes having sufficient length to reach the subcutaneous fat layer allows for such probes to apply energy in the subcutaneous fat layer. Application of the energy can break down the fat cells in that layer allowing the body to absorb the resulting free fatty acids into the blood stream. Such a process can allow for contouring of the body surface for improved appearance. Naturally, such an approach can be used in the reduction of cellulite.

Other possible uses include pain management (both in the use of heat to reduce pain in muscle tissue and by directly ablating nociceptive pain fibers), stimulation of cellular healing cascade via heat, reproductive control by elevated heating of the testicles, and body modification such as scarification.

Figure 1:
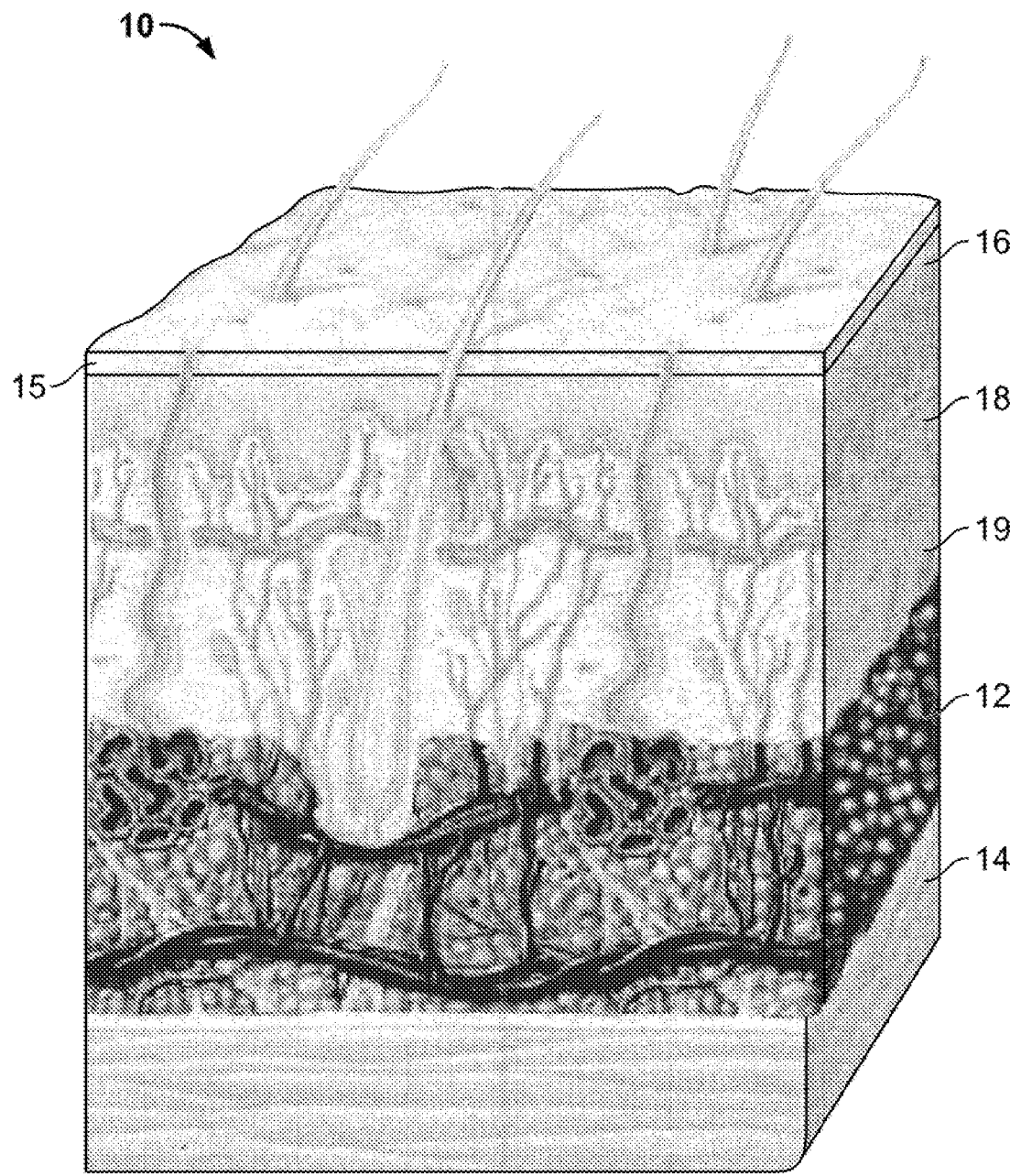
FIG. 1 shows a representative cross sectional view of the skin composed of an outer stratum corneum covering the epidermal and dermal layers of skin and the underlying subcutaneous tissue.

FIG. 1 shows a cross sectional view of the skin 10 composed of an outer stratum corneum 15 covering the epidermis 16. The skin also includes the dermis 18, subcutaneous tissue/fat 12. These layers cover muscle tissue 14 of within the body. In the face and neck areas, the skin 10 measures about 2 mm in cross sectional depth. In the face and neck regions, the epidermis measures about 100 µm in cross sectional depth. The skin 10 also includes a dermis 18 layer that contains a layer of vascular tissue. In the face and neck regions, the dermis 18 measures about 1900 µm in cross sectional depth.

The dermis 18 includes a papillary (upper) layer and a 19 reticular (lower) layer. Most of the dermis 18 comprises collagen fibers. However, the dermis also includes various hair bulbs, sweat ducts, sebaceous glands and other glands. The subcutaneous tissue 12 region below the dermis 18 contains fat deposits as well as vessels and other tissue.

In most cases, when applying cosmetic treatment to the skin for tightening or removal of wrinkles, it is desirable to deliver energy to the dermis layer rather than the epidermis, the subcutaneous tissue region 12 or the muscle 14 tissue. In fact, delivery of energy to the subcutaneous tissue region 12 or muscle 14 may produce pockets or other voids leading to further visible imperfections in the skin of a patient. Also, delivery of excessive energy to the epidermis can cause burns and/or scars leading to further visible imperfections.

The application of heat to the fibrous collagen structure in the dermis 18 causes the collagen to dissociate and contract along its length. It is believed that such disassociation and contraction occur when the collagen is heated to about 65 degree C. The contraction of collagen tissue causes the dermis 18 to reduce in size, which has an observable tightening effect. As the collagen contracts, wrinkles, lines, and other distortions become less visible. As a result, the outward cosmetic appearance of the skin 10 improves. Furthermore, the eventual wound healing response may further cause additional collagen production. This latter effect may further serve to tighten and bulk up the skin 10.

Thermal energy is not the only method for treating collagen in the dermal layer to effect skin laxity and wrinkles. Mechanical disruption or cooling of tissue can also have a desirable therapeutic effect. As such, the devices and methods described herein are not limited to the percutaneous delivery of thermal energy, but also include the percutaneous delivery of mechanical energy or even reducing temperature of tissues beneath the epidermis (e.g., hypothermia effect on tissue).

The treatment methods and device can also include the use of additives, medicines, bioactive substances, or other substances intended to create a therapeutic effect on their own or augment a therapeutic effect created by any one of the energy modalities discussed herein.

For example, autograph or allograph collagen can be delivered percutaneously to bulk up the dermal layer. Non-collagen fillers such as absorbable and non-absorbable polymers can also be delivered to increase the volume of the dermis and improve the surface appearance of the skin. Saline can be delivered to provide a diffuse path for radio frequency current delivery or to add or remove thermal energy from the target tissue. In addition, anesthetic or numbing agents can be delivered to reduce the patient's sensation of pain from the treatment. The agent can be applied on the epidermal layer or can be injected into the dermal layer of the skin. Botulinum Toxin type A (Botox®) can also be delivered to the dermis or to the muscular layer below the dermis by further inserting the access probe 32. The delivery of Botox® can temporarily paralyze the underlying musculature allowing for treatment of the target area with no muscle movement to move or disturb the treatment area.

The delivery of the substances described above can occur using the same delivery devices that apply the energy based treatment. Alternatively, or in combination, a physician can administer such substances using a delivery means separate from the treatment devices.

Figure 2A:
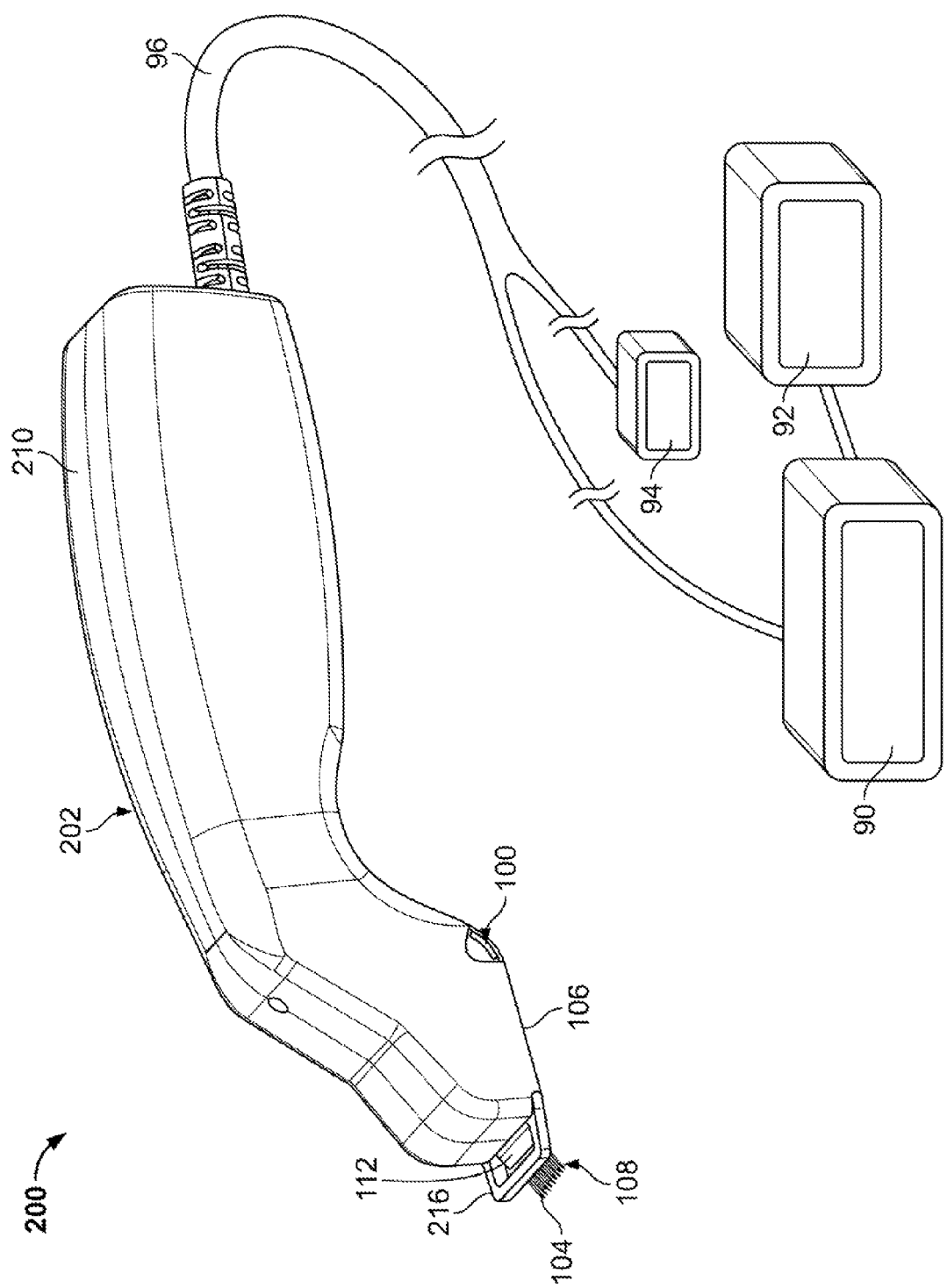
FIG. 2A shows a sample variation of a system according to the principles of the invention having probes configured to provide percutaneous energy delivery.

FIG. 2A illustrates one variation of a treatment system according the principles described herein. The treatment system 200 generally includes a treatment unit 202 having a hand-piece or device body 210 (or other member/feature that allows for manipulation of the system to treat tissue 10) having one or more probes 104 extending from the body 210. In some variations, the probes 104 are coupled to the body 210 via a removable cartridge 100. In the system 200 shown, the removable cartridge 100 contains a plurality of retractable probes 104 arranged in an array 108. The term probes 104 (for purposes of this disclosure) is intended to include any electrode, energy transfer element (e.g., thermal, electrical, electromagnetic, microwave, mechanical, ultrasound, light, radiation, monopolar RF, bipolar RF, chemical, radioactive, etc.), or source of therapeutic treatment. For sake of convenience, the term probe shall be used to refer to any electrode, energy transfer element or source of therapeutic treatment unless specifically noted otherwise. As shown, the probes 104 can optionally extend from a front portion 112 of the cartridge 100. Alternatively, the probes 104 can extend from a front face of the device body or from any surface of the device body/cartridge.

The device body 210 or the cartridge 100 is not limited to that shown. Instead, variations include device body shapes that are thinner in profile and can be held at a more vertical angle to the target tissue like a pencil or pointer. Variations also include a device body that has a loop or curved grip that facilitates one specific manner in which it can be grasped by the hand. Any number of variations is possible especially those that ensure the physician's hand does not contact of the distal end of the cartridge or the target tissue.

The devices according to the principles described herein can include any number of arrays depending upon the intended treatment site. Currently, the size of the array, as well as the number of arrays, can change depending on the variation of the invention needed. In most cases, the target region of tissue drives the array configuration. The present invention allows a physician to selectively change array configuration by attaching different cartridges 100. Alternatively, variations of the invention contemplate an probe assembly that is non-removable from the device body 200.

For example, a treatment unit 202 designed for relatively small treatment areas may only have a single pair of probes. On the other hand, a treatment unit 202 designed for use on the cheek or neck may have up to 10 probe pairs. However, estimates on the size of the probe array are for illustrative purposes only. In addition, the probes on any given array may be the same shape and profile. Alternatively, a single array may have probes of varying shapes, profiles, and/or sizes depending upon the intended application.

Furthermore, the array 108 defined by the individual probes 104 can have any number of shapes or profiles depending on the particular application. As described in additional detail herein, in those variations of the system 200 intended for skin resurfacing, the length of the probes 104 is generally selected so that the energy delivery occurs in the dermis layer of the skin 10 while the spacing of probes 104 may be selected to minimize delivery of energy between adjacent pairs of probes or to minimize energy to certain areas of tissue.

In those variations where the probes 104 are resistive, radiofrequency, microwave, inductive, acoustic, or similar type of energy transfer elements, the probes can be fabricated from any number of materials, e.g., from stainless steel, platinum, and other noble metals, or combinations thereof. Additionally, such probe may be placed on a non-conductive member (such as a polymeric member).

Additionally, the treatment unit 202 may or may not include an actuator as described below for driving the probe array 108 from the cartridge 100 into the target region. Examples of such actuators include, but are not limited to, pneumatic cylinders, springs, linear actuators, or other such motors. Alternative variations of the system 200 include actuators driven by the control system/energy supply unit 90.

FIG. 2A also shows a stabilization plate 234 coupled to the device body 210. As described below, the stabilization plate 214 can serve several functions ranging from securing tissue flatly and in line with the tissue engaging surface 106 to providing cooling of the tissue directly normal to the application of energy. In addition, in some variations the stabilization plate 214 can also provide a visual frame of reference for the physician prior to or during treatment.

As shown, the stabilization plate 214 holds tissue in front of the probe array 108 flat and in place. This prevents the tissue from "bunching" in front of the device and increases the likelihood that the array 108 are inserted a consistent depth within the tissue.

The system 200 also includes an energy supply unit 90 coupled to the treatment unit 202 via a cable 96 or other means. The energy supply unit 90 may contain the software and hardware required to control energy delivery. Alternatively, the CPU, software and other hardware control systems may reside in the hand piece 210 and/or cable 96. It is also noted that the cable 96 may be permanently affixed to the supply unit 90 and/or the treatment unit 202. In additional variations, the hand piece 210 can contain the controls alone or the controls and the power supply necessary to delivery treatment.

In one variation, the energy supply unit 90 may be a RF energy unit. Additional variations of energy supply units may include power supplies to provide or remove thermal energy, to provide ultrasound energy, microwave energy, laser energy, pulsed light energy, and infrared energy. Furthermore, the systems may include combinations of such energy modalities.

For example, in addition to the use of RF energy, other therapeutic methods and devices can be used in combination with RF energy to provide additional or more efficacious treatments. For example, as shown in FIG. 2A, additional energy sources 90 can be delivered via the same or additional energy transfer elements located at the working end of a treatment unit 202. Alternatively, the radiant energy may be supplied by the energy source/supply 90 that is coupled to a diode, fiber, or other emitter at the distal end of the treatment unit 202. In one variation, the energy source/supply 94 and associated energy transfer element may comprise laser, light or other similar types of radiant energy (e.g., visible, ultraviolet, or infrared light). For example, intense pulsed light having a wavelength between 300 and 12000 nm can also be used in conjunction with RF current to heat a targeted tissue. Such associated transfer elements may comprise sources of light at the distal end of the treatment unit 202. These transfer elements may be present on the cartridge 100, on the device body 210 or even on the cooling unity 234. More specifically a coherent light source or laser energy can be used in conjunction with RF to heat a targeted tissue. Examples of lasers that can be used include erbium fiber, $CO_2$, diode, flashlamp pumped, Nd:YAG, dye, argon, ytterbium, and Er:YAG among others. More than one laser or light source can be used in combination with RF to further enhance the effect. For example, a pulsed infra-red light source can be used to heat the skin surface, an Nd:YAG laser can be used to heat specific chromophores or dark matter below the surface of the skin, and RF current can be applied to a specific layer within or below the skin; the combination of which provides the optimal results for skin tightening, acne treatment, lipolysis, wart removal or any combination of these treatments.

Other energy modes besides or in addition to the optical energy described above can also be used in conjunction with RF current for these treatments. Ultrasound energy can be delivered either through the RF probes, through a face plate on the surface of the skin, or through a separate device. The ultrasound energy can be used to thermally treat the targeted tissue and/or it can be used to sense the temperature of the tissue being heated. A larger pulse of pressure can also be applied to the surface of the skin in addition to RF current to disrupt adipose tissue. Fat cells are larger and their membranes are not as strong as those of other tissue types so such a pulse can be generated to selectively destroy fat cells. In some cases, the multiple focused pressure pulses or shock waves can be directed at the target tissue to disrupt the cell membranes. Each individual pulse can have from 0.1 to 2.5 Joules of energy. The ultrasound energy could also be used for imaging purposes. For example, it could be used to assess the penetration depth of the electrodes, or to identify in which tissue layer the electrodes are located.

The energy supply unit 90 may also include an input/output (I/O) device that allows the physician to input control and processing variables, to enable the controller to generate appropriate command signals. The I/O device can also receive real time processing feedback information from one or more sensors associated with the device, for processing by the controller, e.g., to govern the application of energy and the delivery of processing fluid. The I/O device may also include a display, to graphically present processing information to the physician for viewing or analysis.

In some variations, the system 200 may also include an auxiliary unit 92 (where the auxiliary unit may be a vacuum source, fluid source, ultrasound generator, medication source, a source of pressurized air or other gas, etc.) Although the auxiliary unit is shown to be connected to the energy supply, variations of the system 200 may include one or more auxiliary units 92 where each unit may be coupled to the power supply 90 and/or the treatment unit 202.

Figure 2B:
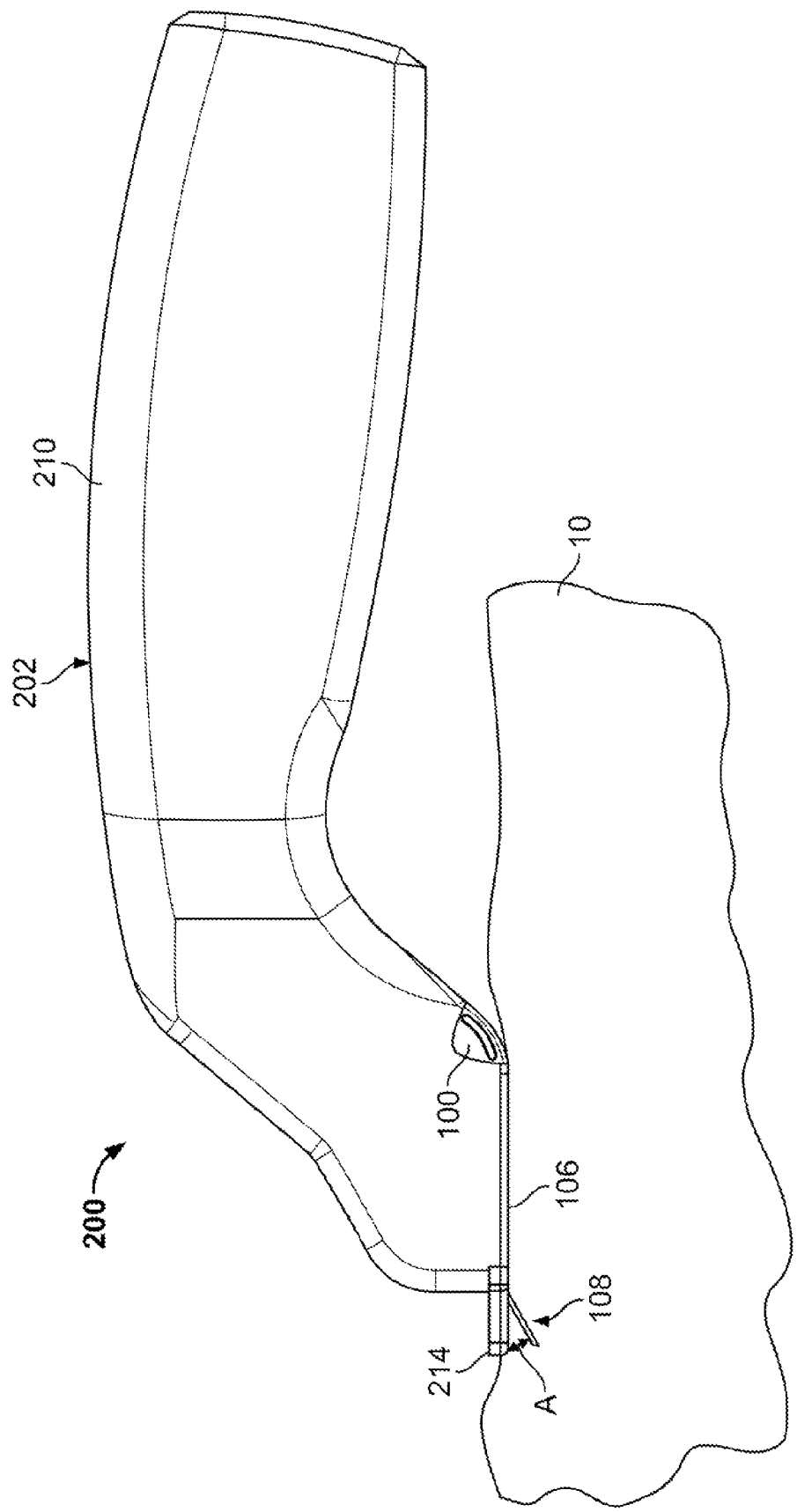
FIG. 2B illustrates a partial view of a working end of a treatment unit where the treatment unit engages against tissue using both a stabilization surface and a tissue engaging surface.

FIG. 2B illustrates a partial view of a working end of a treatment unit 202 where the treatment unit 202 engages against tissue 10 with the tissue engaging surface 106 as well as the stabilization surface 214 smoothing the tissue 106 beneath the device 200 to increase the uniformity of insertion depth of the array 108. As shown, the array 108 can then be inserted into the tissue 10 when advanced from a cartridge 100.

The illustrated figure also demonstrates another feature of the system where the system 200 includes a tissue engaging surface 106 (in this variation on a cartridge 100 having a plane that forms an angle A with a plane of the array of probes 108. As described below, this configuration permits a larger treatment area as well as direct cooling of the tissue surface. The devices of the present invention may have an angle A of 20 degrees. However, the angle can range from anywhere between perpendicular (90 degrees) to quasi-parallel (nearly zero degrees but still able to penetrate tissue) with respect to the tissue surface. The angle A is typically chosen to increase the likelihood that an active portion of the probe will be inserted within a desired location in tissue. Accordingly, the depth of the target region, design of the hand piece, as well as a number of additional factors may require that the angle vary between nearly 0 and 90 degrees.

The tissue engaging surface 106 can also include any number of features to ensure adequate contact with tissue (such as increased frictional characteristics, sensors to ensure proper contact, etc.). It was observed that having a penetration angle of about 20 degrees facilitated the insertion of the needles into the skin tissue layers when compared to a perpendicular penetration angle. Tensioning the skin at the insertion points further facilitated the penetration into tissue. The stabilization surface, in conjunction with the tissue engaging surface 106, can also be used to hold and therefore tension the skin at the insertion points to facilitate the needle insertion in the skin.

Although not shown, the tissue engagement surface may contain apertures or other features to allow improved engagement against tissue given the application of a vacuum. By drawing tissue against the tissue engaging surface the medical practitioner may better gauge the depth of the treatment. For example, given the relatively small sectional regions of the epidermis, dermis, and subcutaneous tissue, if a device is placed over an uneven contour of tissue, one or more probes may be not be placed at the sufficient depth. Accordingly, application of energy in such a case may cause a burn on the epidermis. Therefore, drawing tissue to the tissue engaging surface of the device increases the likelihood of driving the probes to a uniform depth in the tissue.

In such an example, the tissue engagement surface 106 can include small projections, barbs, or even an elastic resin to increase friction against the surface of tissue. These projections or features can grip or provide friction relative to the tissue in proximity of the target tissue. This grip or friction holds the tissue in place while the probes are inserted at an angle relative to the grip of the projections. In another variation, the tissue engaging surface can include contact or proximity sensors to ensure that any numbers of points along the tissue engaging surface are touching the surface of the target site prior to probe deployment and/or energy delivery.

Figure 2C:
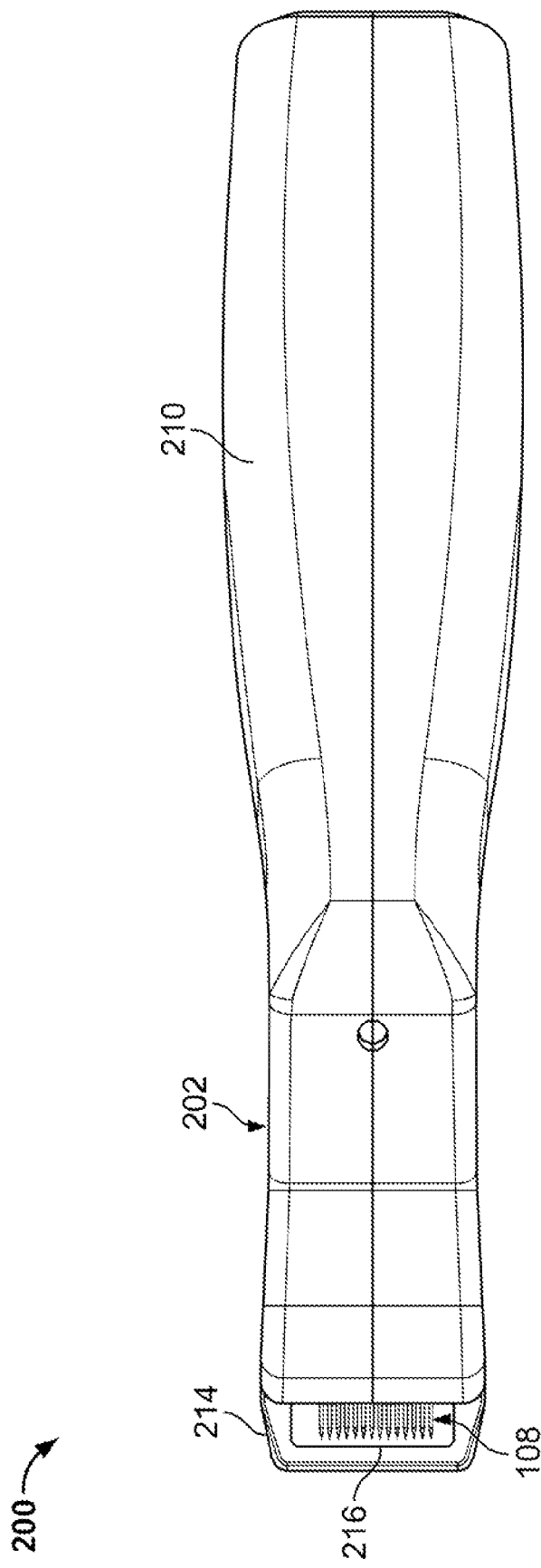
FIG. 2C shows a top view of the treatment unit of FIG. 2B showing a stabilization plate with a feature that permits a physician to directly observe insertion of the probe array.

FIG. 2C shows a top view of the treatment unit 202 of FIG. 2B. In this variation, the stabilization plate 214 includes a feature 216 such as (a window or an opening) that permits a physician to directly observe insertion of the probe array 108 through the stabilization plate 214. In additional variations of the system 200, the stabilization plate 214 can be fabricated to be transparent and the feature 216 can comprise a marking to outline the tissue region in which the probes will be inserted. Such features of the stabilization plate 214 are important when the probes are deployed into tissue subsequent to placement of the device body 210 against tissue. A physician can rely upon the stabilization plate 214 or the feature 216 as confirmation for the intended treatment area and avoid body structures where treatment would be undesirable. For example, if a physician intends to avoid insertion of the probe array 108 into a particular tissue structure, the stabilization plate 214 or feature 216 permits the physician to situate the treatment unit 202 while avoiding the region in question. In certain variations, the outline of the feature 216 or the stabilization plate 214 itself aligns (in a normal plane) with the distal end of the probe array 108.

The electrodes of the probe array can also include any number of visually distinguishing features (e.g., depth markings, colors, shades, etc.) that enable a physician to observe proper placement. For example, a probe can be marked with a certain color that they physician should be able to see during treatment. This ensures that the probe is not driven too far into tissue. Alternatively, the probe can be marked with one or more features that allow the physician to determine the depth of insertion of the probe.

The stabilization plate 214 can also be designed to permit the physician with an outline of the extent of tissue being treated. For example, the entire stabilization plate 214 can be sized to have a profile to correspond to the area of tissue that will affected by the energy supplied to the tissue. Much like the tissue engaging surface, the stabilization plate 214 can have any number of projections, points, barbs, hooks, vacuum or fluid apertures to further stabilize tissue.

Figure 3A:
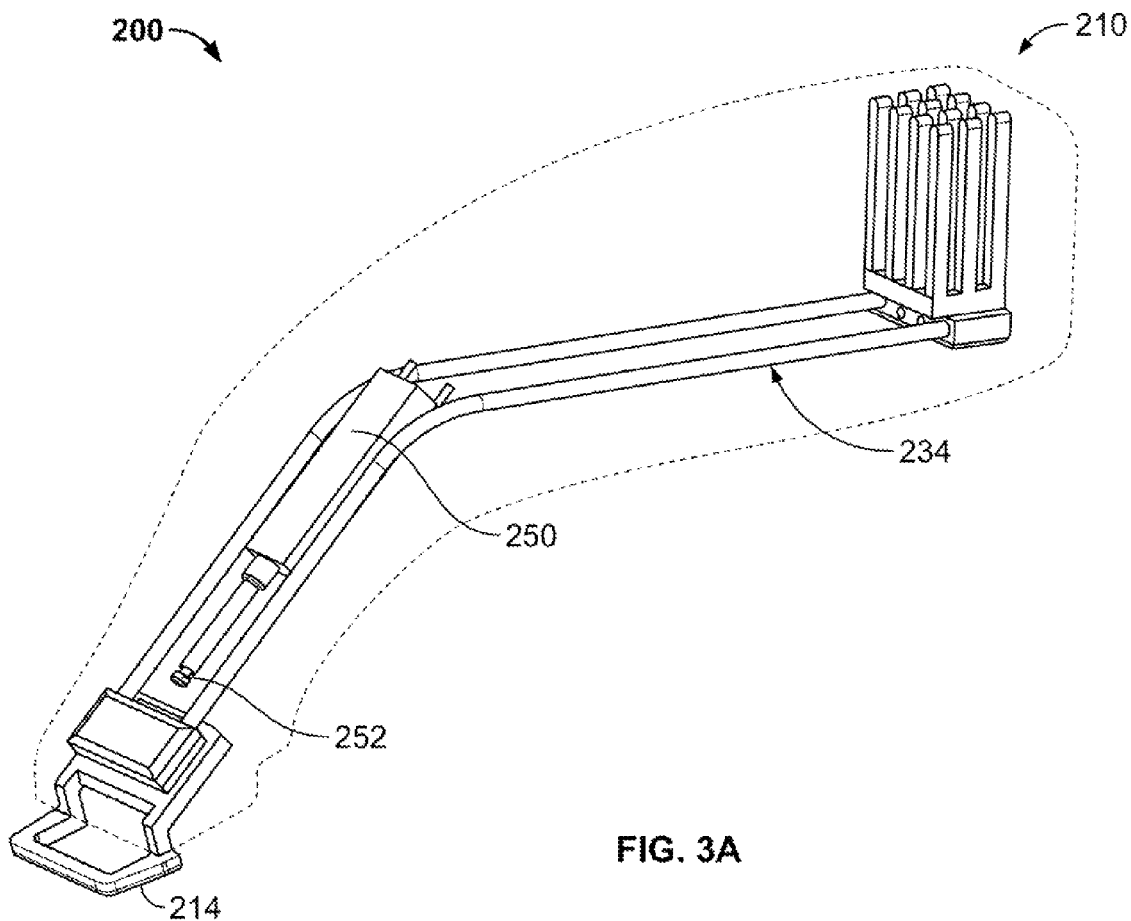
FIG. 3A illustrates a sectional perspective view of a treatment unit for use with the systems described herein.

FIG. 3A illustrates a sectional view of a device body 210 to illustrate placement of an actuator 250 and a cooling device 234 within the device body 210. For purposes of clarity, some of the components of the device body 210 are omitted.

As shown, the system 200 can include an actuator 250 within the device body 210 that can be coupled to an array of probes in a mating receiving surface (discussed below) to drive the probes into tissue. The actuator 250 can be coupled to the array at a distal end of a shaft 252 in any commonly known manner. In this variation, the actuator 250 comprises a motor or drive unit that provides sufficient force, speed or impact to the probes to drive them into tissue. In certain variations, the actuator 250 can be spring loaded to deliver sufficient force, speed or impact to allow penetration of the probe array into tissue. However, the actuator may comprise any number of actuation means, including, but not limited to, pneumatic cylinders, springs, linear actuators, or other such motors.

Figure 2D:
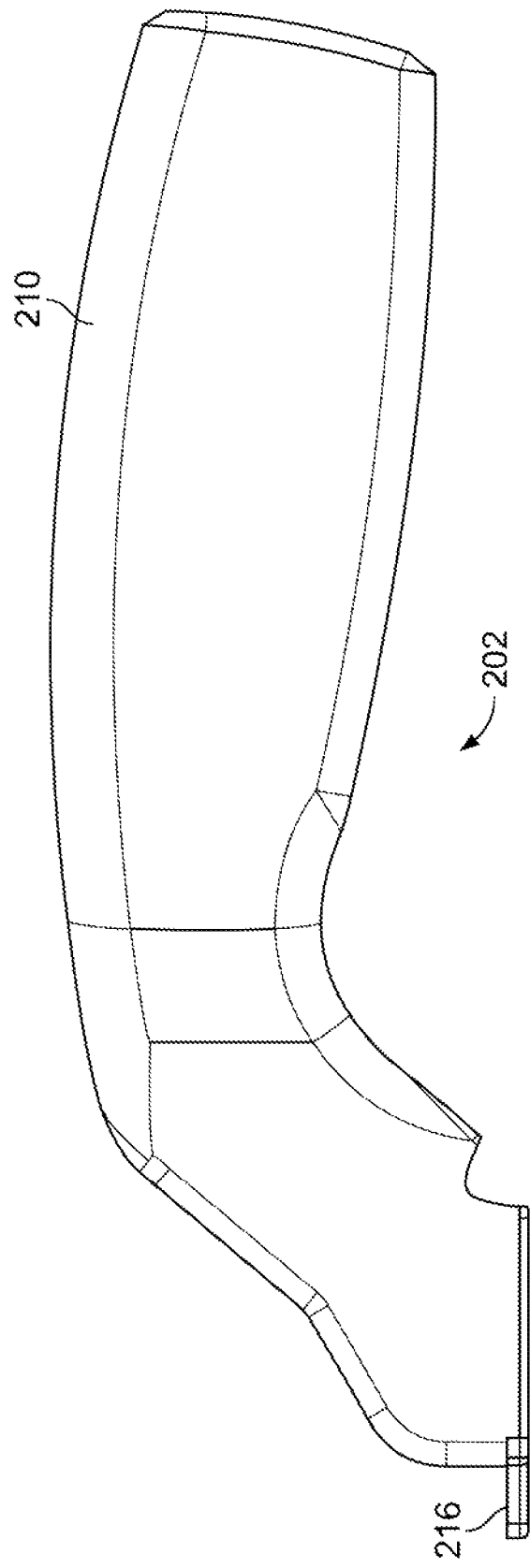
FIG. 2D shows the treatment system of FIG. 2A where the cartridge assembly and device body are detachable.
Figure 2D:
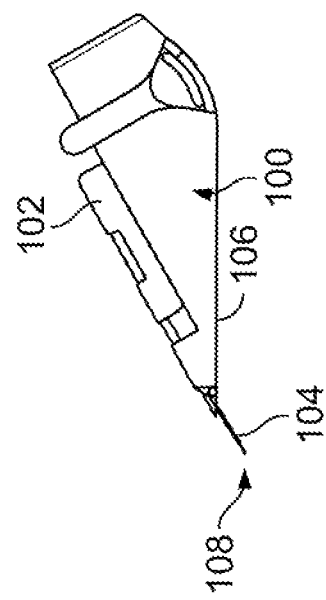

FIG. 2D shows the treatment system 202 of FIG. 2A where the cartridge assembly 100 and device body 210 are separated. In alternate variations, the cartridge body 100 and device body 210 can be a single non-detachable structure. As noted below, a single device body 210 can be used with a variety of cartridge assemblies where each cartridge assembly is specifically configured depending upon the desired application. In most cases, the cartridge assembly 100 places the probes 104 in an array 108 and at a specific orientation relative to a tissue engaging surface 106. The cartridge 100 can also be configured to provide the probes 104 on a probe assembly 102 that is slidable relative to the cartridge body 100 and device body 210 such that the probes 104 can be driven into tissue as further discussed below.

FIG. 3A also illustrates a cooling device 234 for use with the systems described herein. In this variation, the cooling device 234 is fitted within the handle 202 and coupled to the stabilization plate 214. As described below, the cooling device 234 maintains a surface of the tissue being treated at a desired temperature. In this manner, the stabilization plate 214 serves multiple functions (to maintain tissue parallel to the tissue engaging surface 106, to provide a visual boundary for the treatment, and to provide cooling of tissue immediately normal to the treatment region).

Figure 3B:
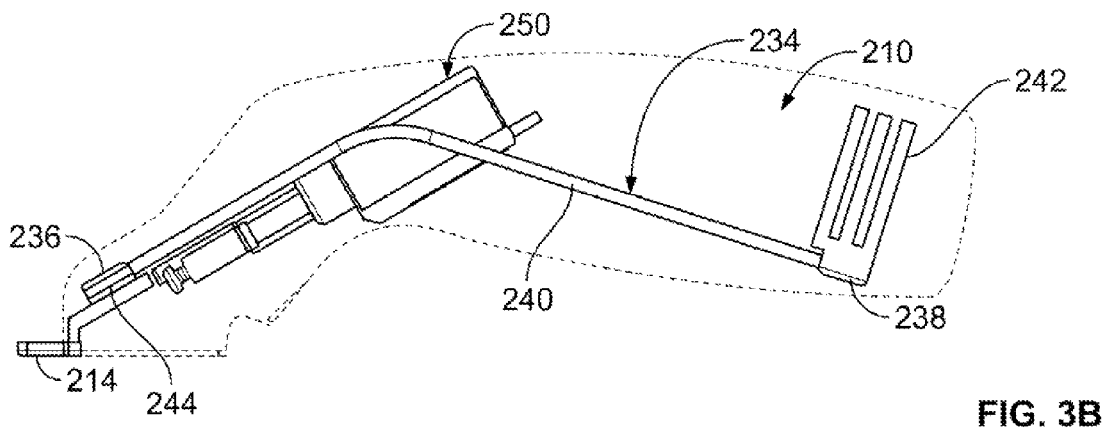
FIG. 3B shows a sectional side view of the treatment unit of FIG. 3A.

FIG. 3B illustrates a side view of the device body 210 from FIG. 3A. As shown, this particular variation of a cooling device 234 permits transfer of heat from a first conduction plate 236 to a second conduction plate 238 via thermal heat pipes 240. Such a configuration permits the first conduction plate 236 to draw heat from the stabilization plate 214. The heat pipes 240 draw heat away from the first conduction plate 236 towards the second conduction plate 238, which is cooled via a heat sink 240. Though not illustrated, the device body 210 can include any number of cooling means (such as fans, fluid sources, etc.) to reduce a temperature of the heat sink 240.

Figure 3C:
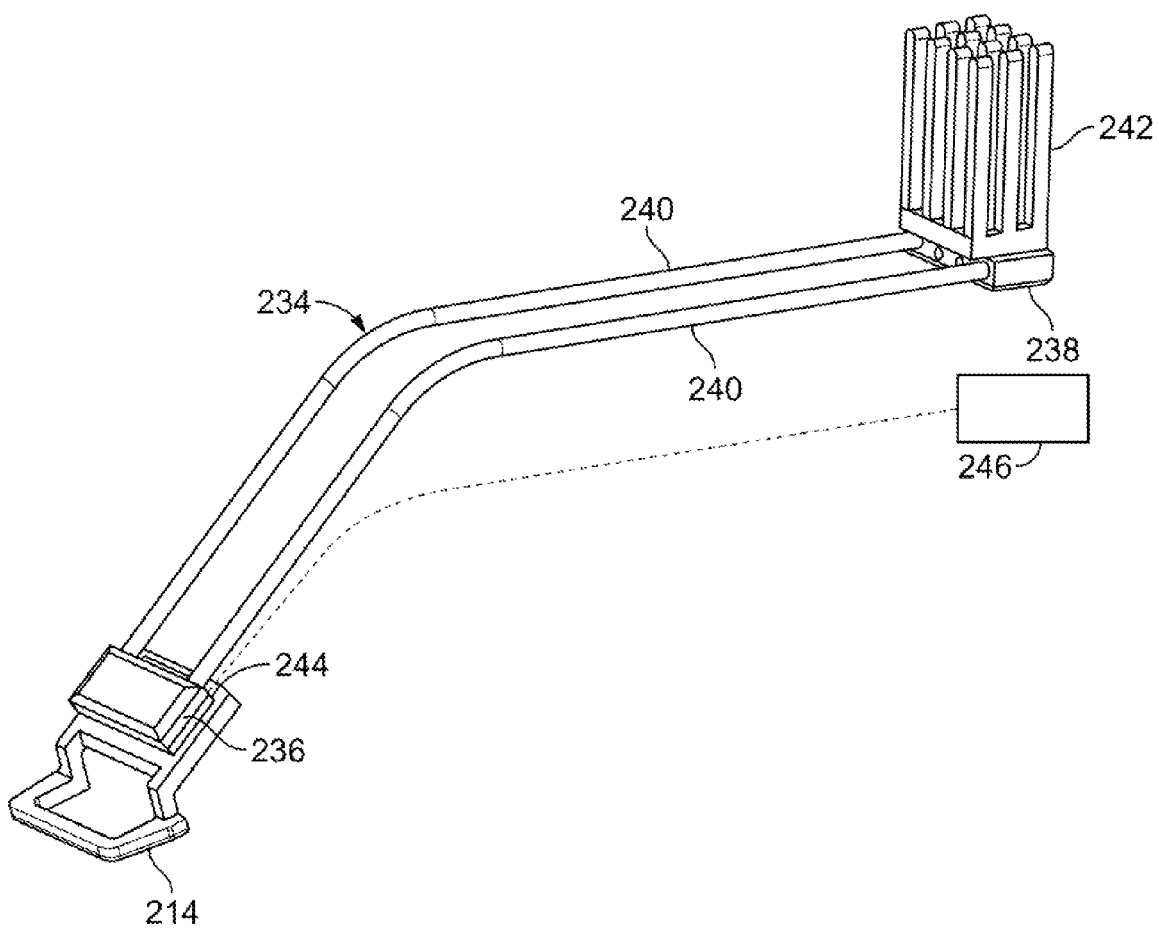
FIG. 3C shows an isometric view of only a cooling device coupled to a stabilization plate.

FIG. 3C shows an isometric view of only a cooling device 234 coupled to a stabilization plate 214. As noted above, the use of heat pipes 240 enables heat to be transported away from the stabilization plate 214 and to a heat sink 242. Such a feature eliminates the need to place the cooling device 234 or portions thereof over the stabilization plate 214. This configuration permits a physician to have unobstructed view of the stabilization surface 214 since the cooling device 234 can be distributed over the length of the handle.

The cooling device 234 can be coupled to a cooling engine (e.g., a source of cooling fluid, a fan, and/or a Peltier device) to assist in maintaining the stabilization plate at a desired temperature. For example, a cooling engine 244 can be placed between the first conduction plate 236 and the stabilization plate 214 to maintain the stabilization plate 214 at the desired temperature while the first conducting plate 236 draws heat. As shown, the cooling engine 244 can be coupled to a cooling supply 246. For example, the cooling supply can be a power supply for a thermo-electric cooling engine. In an additional variation, the cooling supply 246 can circulate fluid within a cooling engine.

The cooling device can be an air or liquid type cooling device. Alternatively, as noted above, the cooling device can include a Peltier cooling device, which can eliminate the need for a fluid source. In some cases, the cooling device can be powered using the same power supply that energizes the probes. Such a configuration provides a more compact design that is easier for a medical practitioner to manipulate.

Figure 3D:
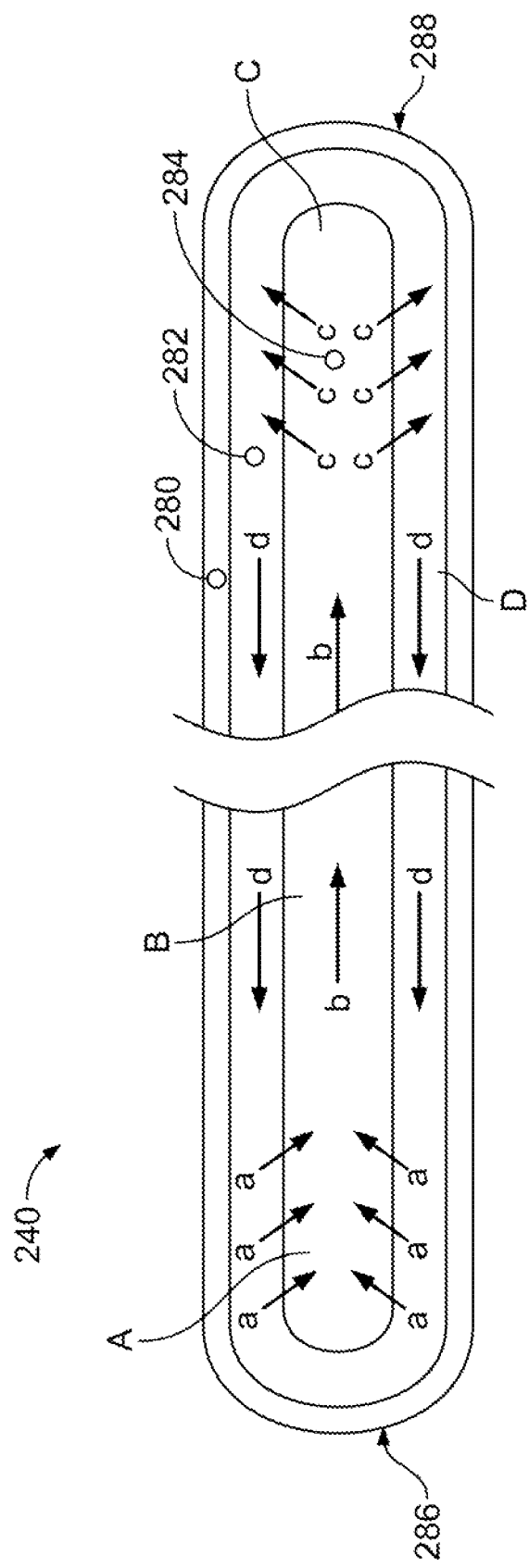
FIG. 3D shows a cross sectional view of a heat pipe for use with the cooling systems described herein.

FIG. 3D shows a cross sectional view of a heat pipe 240 for use with the cooling systems described herein. The heat pipe 240 is comprised of an outer casing 280 comprised of a thermally conductive material such as aluminum, stainless steel, copper, silver, gold, etc. The casing encloses a wick material 282 that defines a chamber 284. A thermally conductive fluid (e.g., water, alcohol, ammonia, etc.) circulates within the heat pipe 240. In step A, a hot end 286 of the heat pipe 240, conducts thermal energy through the casing 280 to the fluid in the wick 282. The fluid evaporates (as denoted by arrow a) from the wick into the chamber 284. In Step B, the vapor migrates (as denoted by arrow b) through the chamber 284 to the cold end 288 of the heat pipe 240. In step C the vapor condenses (as denoted by arrow c) and is absorbed into the wick completing the thermal energy transfer. In step D the fluid is transported (as denoted by arrow d) through the wick 282 back to the hot end 286 of the heat pipe 240 while the thermal energy is conducted out of the casing 280.

In an alternate variation, a cooling engine 244 can be coupled to the second conduction plate 238 to provide a smaller profile towards the stabilization plate 214. In an additional variation, the cooling engine 244 can take the place of the cooling pipes 240 as well as the first and second conduction plates 236, 238.

Figure 4A:
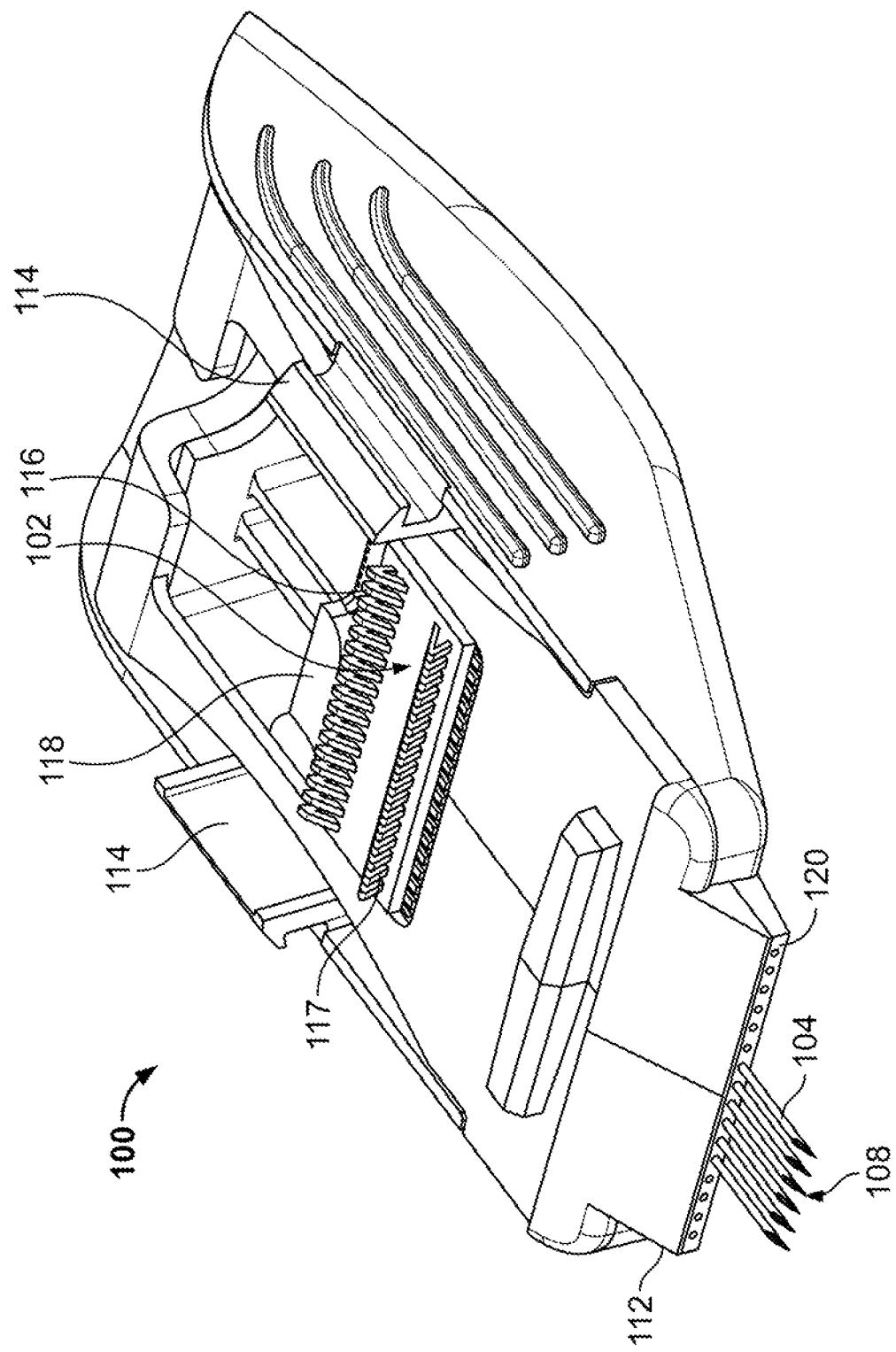
FIGS. 4A and 4B show variations of cartridge bodies for use with variations of the present system.

FIG. 4A illustrates one variation of a cartridge body 100 for use with variations of the present system. As shown, the cartridge body 100 includes retention fasteners 114 allowing for coupling with the device body as well as removal from the device body. Again, any number of structures can be incorporated into the device to permit removable coupling of the cartridge body 100 to a treatment unit.

The cartridge body 100 further includes an electrode assembly 102 that is moveable or slidable within the cartridge body 100. The mode of movement of the actuator can include those modes that are used in such similar applications. Examples of these modes include, sliding, rotation, incremental indexing (via a ratchet-type system), stepping (via an step-motor) Accordingly, the electrode assembly 102 can include a coupling portion or structure 118 that mates with an actuating member in the device body. In the illustrated example, the electrode assembly 102 is in a treatment position (e.g., the array 108 extends from the cartridge 100 allowing for treatment). The electrode assembly 102 includes any number of electrodes 104 that form an array 108 and are extendable and retractable from a portion 104 of the cartridge 100 (as noted above, the electrodes can alternatively extend from the device body, or other parts of the system). As noted above, although the illustrated example shows an array 108 of 1×6 electrodes 104, the array can comprise any dimension of M×N electrodes where the limits are driven by the nature of the treatment site as well as the type of energy delivery required.

FIG. 4A also shows the electrodes 104 in the electrode assembly 102 as having connection or contact portions 116 that couple to a connection board on a treatment unit to provide an electrical pathway from the power supply to the electrodes 104. In the illustrated variation, the electrode assembly 102 as well as the connection portions 116 moves. Such a feature allows for selective connection of the electrodes with the power supply. For example, in certain variations of the system, the electrodes are only coupled to the power supply when in a treatment position and are incapable of delivering energy when in a retracted position. In another variation, the electrode assembly and connection board are configured to permit temperature detection at all times but only energy delivery in the treatment position. Such customization can prevent energy delivery in an unintended location, for example, when the electrodes have an insulation that only allows energy delivery at the distal tip and the intended location of energy delivery is at specific depth in the target tissue that corresponds to the length of the extended electrode the electrode cannot delivery energy to an unintended shallower location when it is not fully extended. However, any number of variations is possible. For example, the system can be configured so that the electrodes can be energized whether in the treatment or retracted positions.

The connection portions 116 can be fabricated in any number of configurations as well. For example, as shown, the connection portions 116 comprise spring contacts or spring pins of the type shown. Accordingly, the connection portions 116 can maintain contact with a corresponding contact point trace on a connection board during movement of the electrode assembly 102

FIG. 4A also shows a front portion 112 of the cartridge 100 as having multiple guiding channels 120. These channels 120 can support and guide the electrode 104 as they advance and retract relative to the cartridge 100. The channels 120 can also be configured to provide alternate energy treatments to the surface of the tissue as well as suction or other fluids as may be required by a procedure. One benefit is that a single cartridge design can be configured to support a variety of electrode array configurations. For example rather than the array of six (6) electrodes as shown, the channels 120 can support any number of electrodes (the illustrated example shows a maximum of sixteen (16) but such a number is for exemplary purposes only). Furthermore, the channels 120 need not be only in a linear arrangement as shown, but could be in 1, 2, 3 or more rows or in a random configuration.

In certain variations of the device, the electrodes can be designed to intentionally "over-insert" and then slightly retract prior to initiating the treatment. This feature allows for improved consistency of complete insertion. The skin can move away on insertion if the skin is not taught resulting in partially inserted electrodes. Over inserting and then partially retracting the electrodes compensates for the movement and laxity of the skin resulting in a more reliable insertion.

Figure 4B:
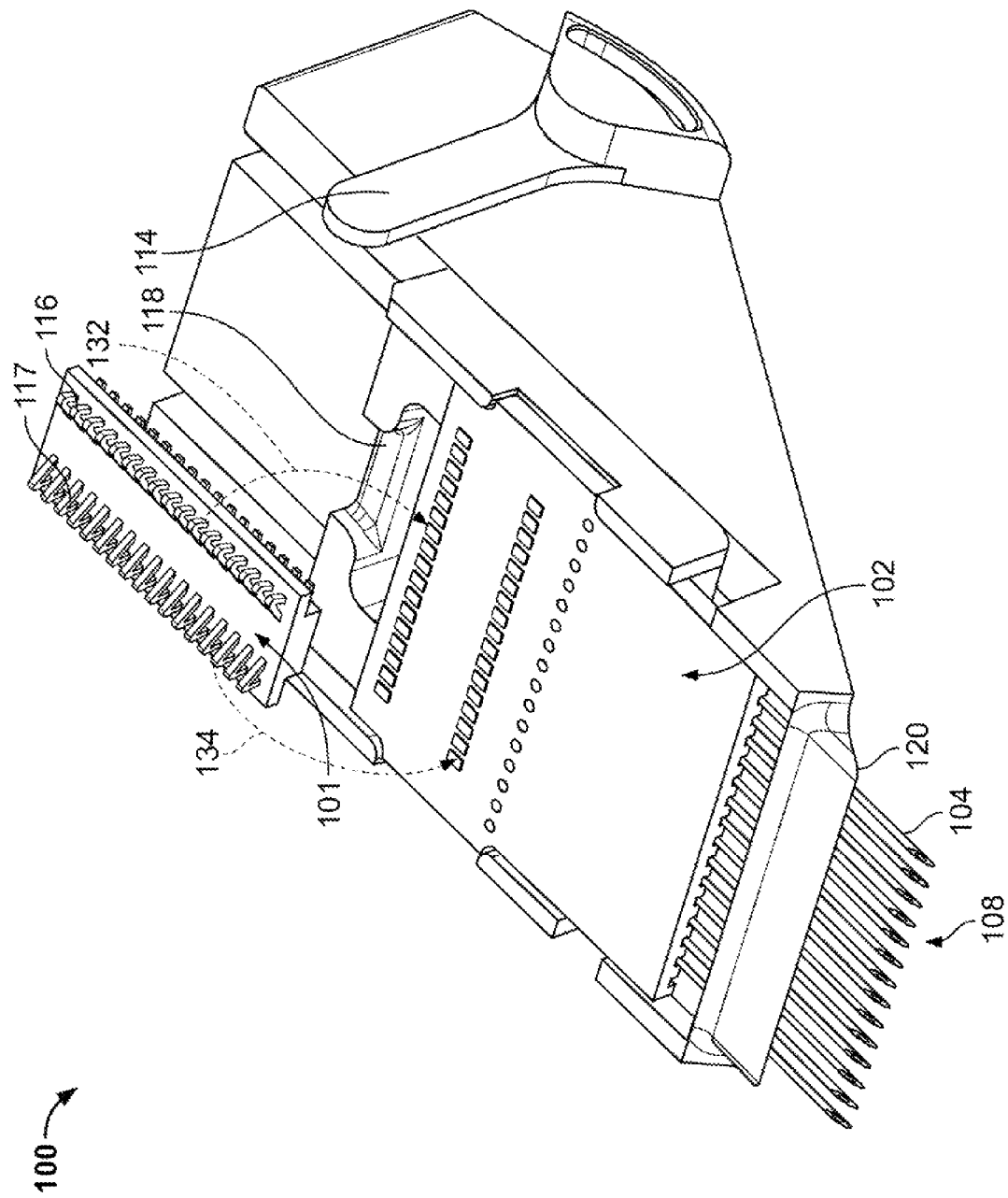

FIG. 4B slows another variation of a cartridge 100. In this variation, the retention fasteners 114 of the cartridge 100 differ from those shown in FIG. 4A. However, any number of connection fastener configurations can be used with various cartridge assemblies of the present invention. FIG. 4B also shows a variation where a connector assembly 101 containing connection portions 116, 117 is separated from the electrode assembly 102. As shown, any type of electrical connection 132, 134 can be used to couple the connecting assembly 101 to the electrode assembly 102. For example, wires, ribbons, etc. can be used. This configuration permits the connection portions 116, 117 to remain stationary while the electrode assembly 102 and probes 104 are slidable within the cartridge 100. As with other variations of cartridge bodies 100 having slidable probes, the cartridge 100 includes a coupling portion 118 to couple the probe assembly to the actuator as discussed below.

Figure 4C:
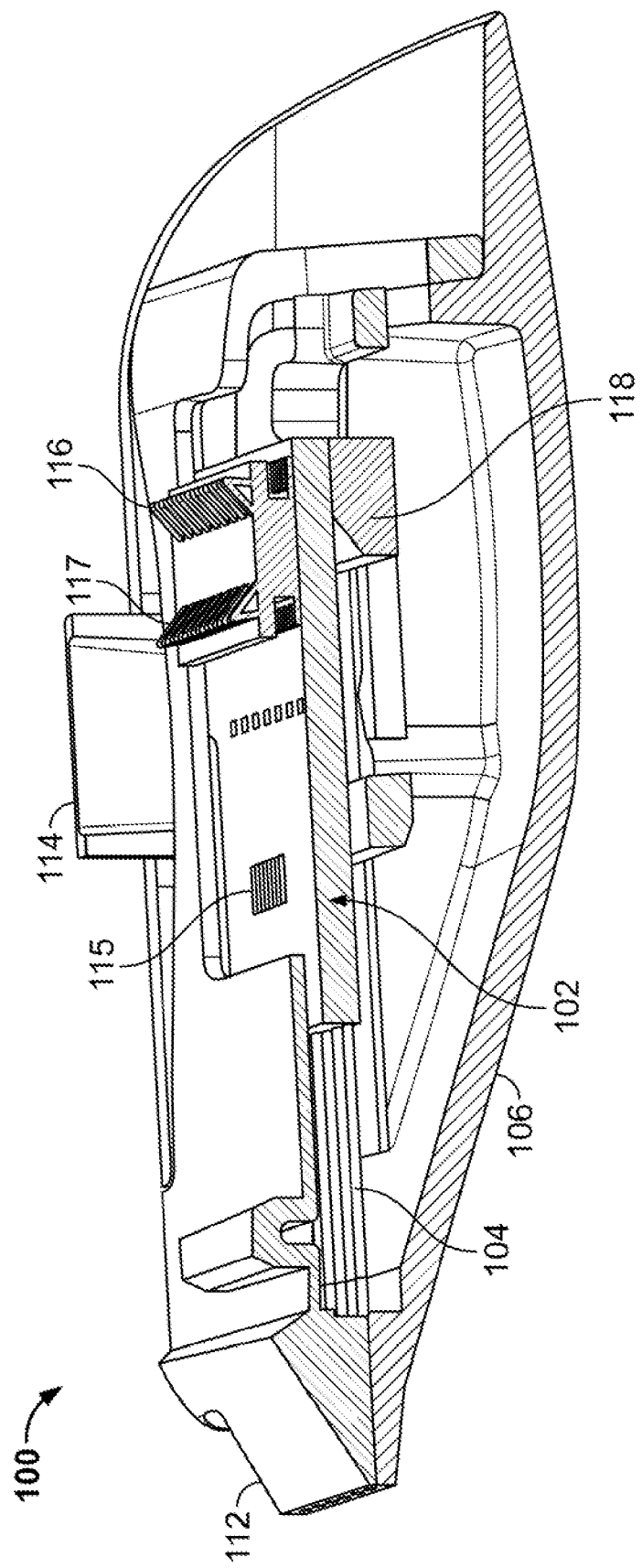
FIG. 4C illustrates a variation of a cartridge body when the electrode assembly 102 is in a retracted position.

FIG. 4C illustrates a variation of a cartridge body 100 when the electrode assembly 102 is in a retracted position. As shown, the connection portions 116, 117 of the electrodes 104 can extend from a top of the electrode assembly 102. The electrode assembly 102 can also optionally include a coupling body 118 to engage an actuator on the treatment device. In this variation, the electrode assembly 102 can have multiple connection portions 116, 117 per individual electrode. In such a case, the multiple connection portions 116 and 117 can be electrically insulated from one another to increase the number of configurations possible with the electrode assembly. For example, and as illustrated below, in one possible variation, the proximal connection portion 116 can electrically couple to a temperature detecting circuit on the hand unit. The distal connection portion 117 can connect to a power delivery circuit only upon distal advancement of the needle assembly 102. In such an example, the temperature of the electrodes can be continuously monitored while the power delivery to the electrodes can be limited to distal advancement of the assembly.

In another aspect of the device, FIG. 4C also shows an example of an electronic memory unit 115, as noted above. The memory unit can provide the system with memory capabilities for containing instructions or record communication between the cartridge and hand unit and/or controller to adjust treatment parameters, monitor usage, monitor sterility, or to record and convey other system or patient characteristics. As also noted above, the unit 115 can also be an RFID antenna or receiver.

Figure 4D:
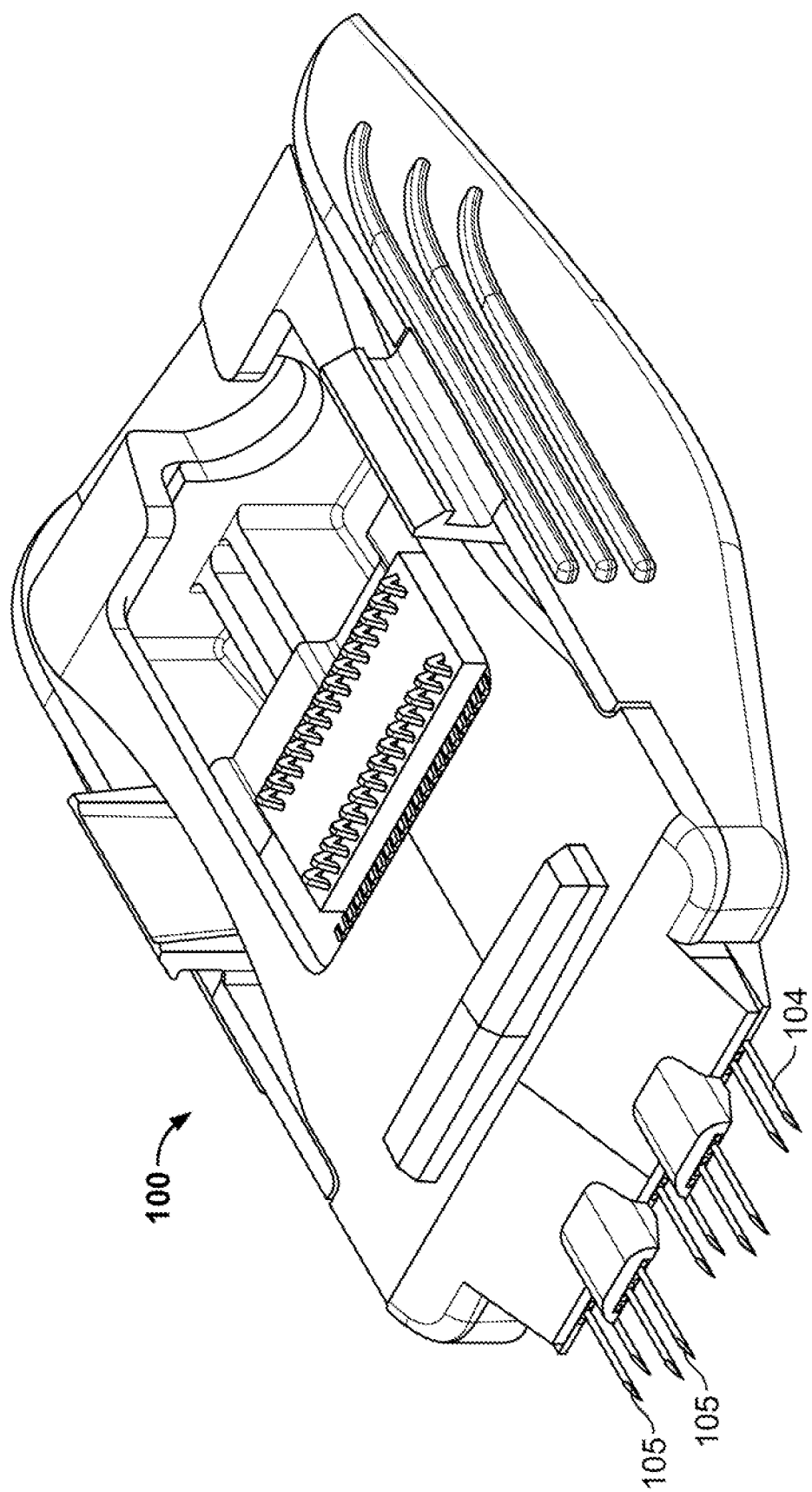
FIG. 4D shows a perspective view of another variation of an electrode assembly having electrodes or probes in a staggered or offset configuration such that adjacent electrode/probe pairs do not form a visible linear pattern when treating tissue.

FIG. 4D shows a perspective view of another variation of an electrode assembly. In this variation, the electrodes 104 are staggered or offset such that adjacent electrode pairs 105 do not form a linear pattern. One such benefit of this configuration is to overcome the creation of a "line effect" in tissue. For example, an array of electrodes arranged in a single line can possibly result in a visible line in tissue defined by the entry points of adjacent and parallel electrodes. In the variation of FIG. 4D, staggering or offsetting the electrodes prevents the "line effect" from occurring.

Figure 4E:
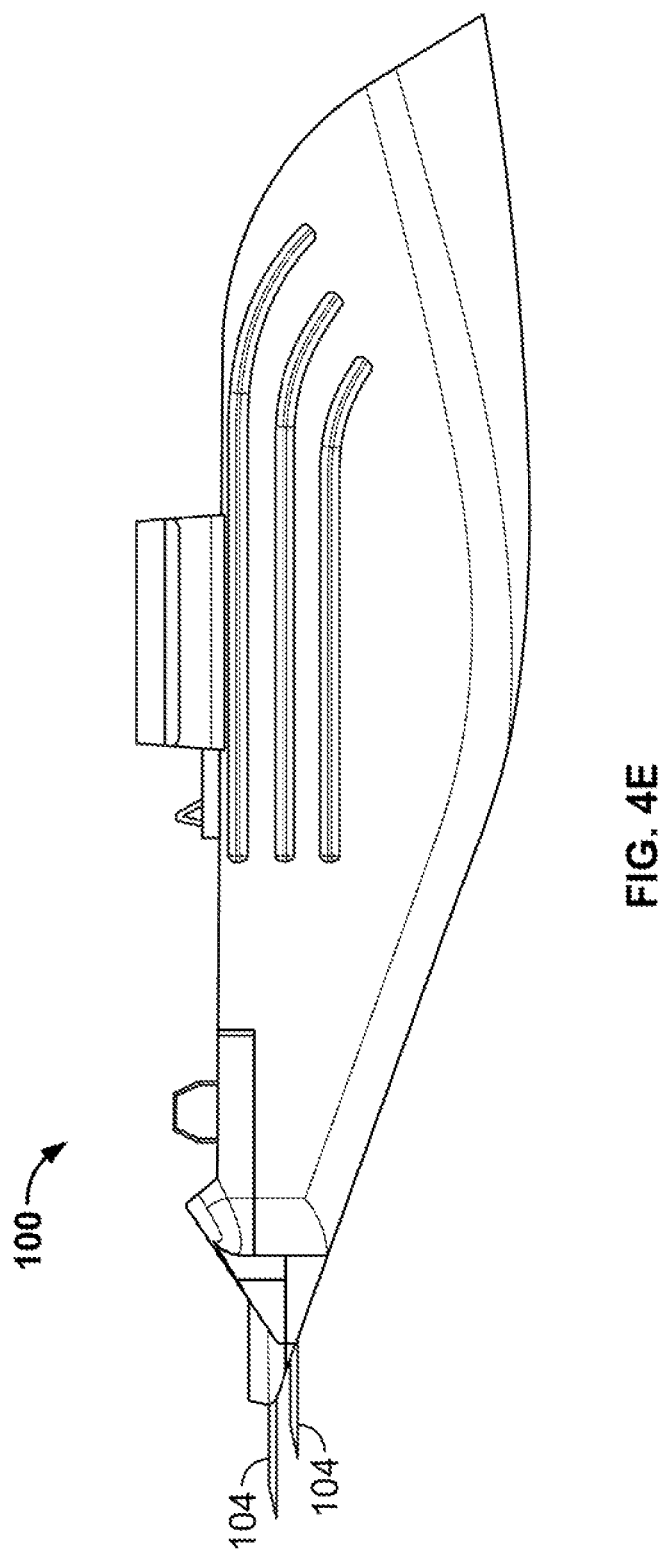
FIG. 4E shows a side view of the variation of FIG. 4D.

FIG. 4E shows a side view of the variation of FIG. 4D. As shown, the electrodes 104 are offset to minimize the chance of forming a single continuous line in tissue by penetration of a set of linearly arranged electrodes and therefore maintaining the focal and fractional aspect of the created lesions, as further explained in FIGS. 11A and 11C later in this document. Clearly, other configuration can also address the "line effect". For example, the spacing between adjacent electrodes can be increased to minimize a "line effect" but to still permit efficacy of treatment. In addition, although the illustrated example shows two lines of electrodes, variations of the device include electrodes 104 that form more than two rows of electrodes.

Figure 4F:
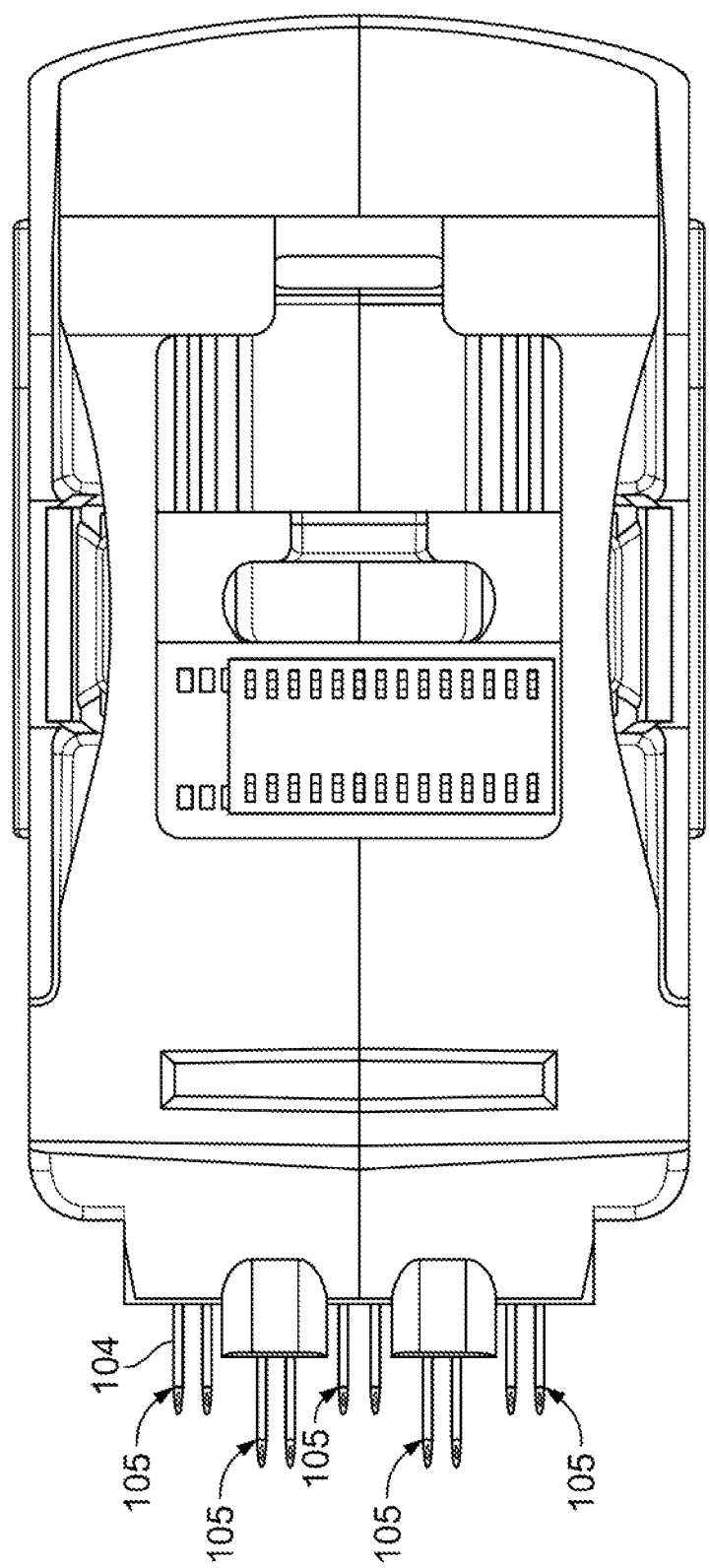
FIG. 4F shows a top view of the cartridge variation of FIG. 4D.

FIG. 4F shows a top view of the cartridge variation of FIG. 4D. The variation illustrated shows that the plurality of electrodes comprises a plurality of electrode pairs 105. As noted above, the electrode pairs 105 can be vertically offset from an adjacent electrode pair (as shown in FIG. 4E) so that insertion of electrode pairs into the tissue does not create a continuous line of insertion points. Moreover, and as shown in FIG. 4F the electrodes 104 can be axially offset (such that an end of the electrode) extends a greater distance than an end of an adjacent electrode or electrode pair. As noted herein, axially offsetting the electrodes allows for a uniform insertion depth when measured relative to a tissue engaging surface of the cartridge.

In one variation, each electrode pair 105 can include an active and return electrode 104 to contain current flow between electrodes in an electrode pair 105. Alternatively, additional configurations are within the scope of the device. For instance, adjacent electrode pairs can serve as opposite poles of a circuit or the electrodes can be monopolar where the therapeutic effect is controlled by selective firing of electrodes. In additional variations, the system can be provided with a number of electrode cartridges where the spacing or offset of the electrodes varies and allows for the physician to control treatment or placement of the electrodes by exchanging cartridges.

As noted above, when provided using a RF energy modality, the ability to control each electrode pair on a separate channel from the power supply provides additional benefits based on the impedance or other characteristic of the tissue being treated. For example, each electrode pair may include a thermocouple to separately monitor each treatment site; the duration of the energy treatment may be controlled depending on the characteristics of the surrounding tissue; selective electrode pairs may be fired rather than all of the electrode pairs firing at once (e.g., by firing electrode pairs that are located on opposite ends of the electrode plate one can further minimize the chance that a significant amount of current flows between the separate electrode pairs.) Naturally, a number of additional configurations are also available depending on the application. Additional variations of the device may include electrode pairs that are coupled to a single channel of a power supply as well.

Figure 5:
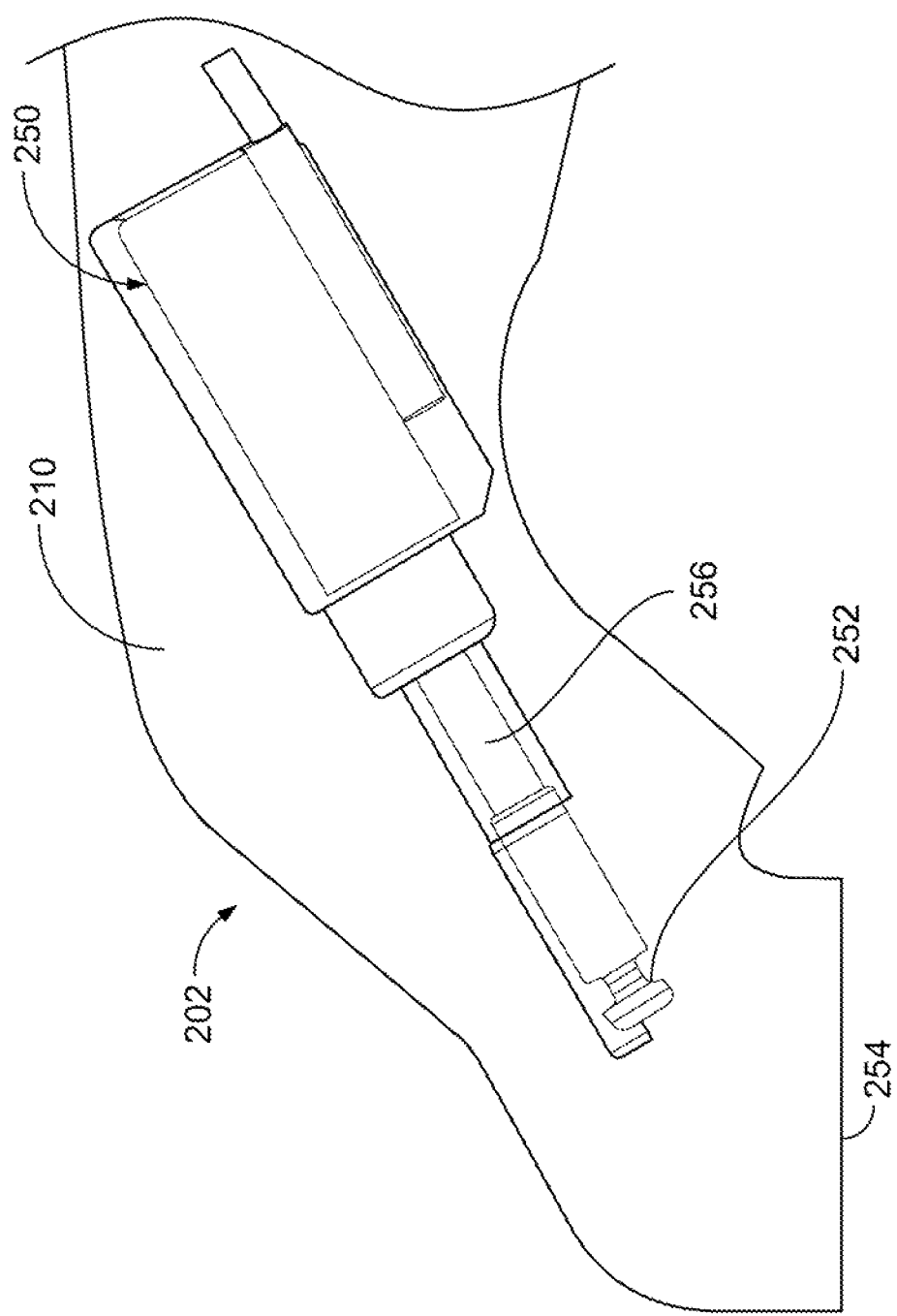
FIG. 5 illustrates a cross sectional view of a distal end of a variation of treatment unit showing a moveable actuator adjacent to the cartridge receiving surface.

FIG. 5 illustrates a cross sectional view of a distal end of a variation of treatment unit 202 without a cartridge attached to a cartridge receiving surface 254 of the device body 210. As shown, the device body 210 includes a moveable actuator 250 adjacent to the cartridge receiving surface 254. In this variation, a shaft 256 of the actuator 250 couples to a cartridge or probe assembly on a cartridge. The actuator 250 moves the shaft 256 where an engagement portion 252 on the shaft couples to the probe assembly (e.g., via a coupling portion 118 shown above) to advance and retract the probes (not shown). In some variations, the actuator can comprise a spring mechanism (not shown) such that it may be spring loaded to deliver sufficient force to cause penetration of a probe array into tissue. However, as noted above, the actuator may comprise any number of actuation means, including, but not limited to, pneumatic cylinders, springs, linear actuators, or other such motors.

Commonly assigned U.S. patent application Ser. Nos. 12/025,924 filed on Feb. 1, 2008 entitled CARTRIDGE ELECTRODE DEVICE and 12/055,528 filed on Mar. 25, 2008 entitled DEVICES AND METHODS FOR PERCUTANEOUS ENERGY DELIVERY, the entirety of each of which is incorporated by reference herein, include additional details of cartridge assemblies and device configurations for use with the systems described herein.

The present systems may apply treatments based upon sensing tissue temperature conditions as a form of active process feedback control. Alternatively, those systems relying on conduction of energy through the tissue can monitor changes in impedance of the tissue being treated and ultimately stop the treatment when a desired value is obtained, or stop the treatment when a maximum allowable impedance value is reached. In another variation, the delivery of energy can depend on whether impedance is within a certain range. Such impedance monitoring can occur before, during, or in between energy delivery and attenuate power if the dynamically measured impedance starts to exceed a given value or if the rate of increase is undesirably high. Yet another mode of energy delivery is to provide a total maximum energy over a duration of time. Still another mode is to provide a maximum output power to limit the power delivery during the application in order to stay within a safe and effective energy delivery mode.

In an additional variation, the controller can adjust the maximum parameters (maximum voltage, maximum current, maximum power, maximum impedance, maximum applied energy), and/or target parameters such as the target temperature or the time at target temperature based on the location of where the energy application is being performed. For example, energy application and/or parameters may vary when the treatment is applied to a face as opposed to a neck of a patient. Clearly, such parameters and/or energy will vary depending on the anatomy of the target tissue (e.g., thicker or thinner tissue, presence of blood vessels, etc.) as well as the therapeutic effect desired.

As noted herein, temperature, impedance, or other sensing may be measured beneath the epidermis in the dermis region. As shown above, each probe may include a sensor or a sensor can be placed on a probe-like structure that advances into the tissue but does not function as an energy delivery probe. In yet another variation, the sensors may be a vertically stacked array (i.e. along the length of the probe) of sensors to provide data along a depth or length of tissue.

Applying the therapeutic treatment in the dermal layer produces a healing response caused by thermally denaturing the collagen in the dermal layer of a target area. As noted herein, systems according to the present invention are able to provide a desirable effect in the target area though they use a relatively low amount of energy when compared to systems that treat through the epidermis. Accordingly, systems of the present invention can apply energy in various modes to improve the desired effect at the target area.

In one mode, the system can simply monitor the amount of energy being applied to the target site. This process involves applying energy and maintaining that energy at a certain pre-determined level. This treatment can be based on a total amount of energy applied and/or application of a specific amount of energy over a set period of time. In addition, the system can measure a temperature of the target site during the treatment cycle and hold that temperature for a pre-determined amount of time. However, in each of these situations, the system does not separate the time or amount of energy required to place the target site in the desired state from the time or amount of energy required to hold the target site in the desired state. As a result, the time or amount of energy used to place the target in a desired state (e.g., at a pre-determined temperature) is included in the total treatment cycle. In some applications, it may be desirable to separate the portion of the treatment cycle required to elevate the target to a pre-determined condition from the portion of the treatment cycle that maintains the target site at the pre-determined conditions.

For example, in one variation, the system can maintain a temperature of the target site at a pre-determined treatment temperature during a pre-determined cycle or dwell time. The system then delivers energy to maintain the target site at the treatment temperature. Once the target site reaches the treatment temperature, the system then maintains this condition for the cycle or dwell time. This variation allows for precise control in maintaining the target site at the pre-determined temperature. In another variation, the system can monitor the amount of power applied to the target site for a specific dwell time. By continuously measuring current and output voltage, the system can calculate both the impedance changes and the delivered power levels. With this method a specific amount of power can be delivered to the target tissue for a specified amount of time. In addition, the above variations can be combined with various methods to control time, temperature or energy parameters to place the tissue in the desired state. For example, the system can employ a specified ramp time or maximum energy to achieve the pre-determined treatment temperature. Such a variation can create a faster or slower ramp to the treatment temperature.

Although the treatment of tissue generally relies on energy to affect the tissue, the mere act of inserting the probe array into tissue can also yield therapeutic benefits. For instance, the mechanical damage caused by placement of the probes also produces an adjunct healing response. The healing response to injury in the skin tissue can contribute to the production of new collagen (collagenesis) that can further improve the tone or appearance of the skin. Accordingly, in one variation a medical practitioner may opt to use the methods and systems to create mechanical injury to tissue by placing probes into target areas without thermal treatment to induce a healing response in the targeted area. Accordingly, the invention is not limited to application of energy via the probes.

The low energy requirements of the system present an additional advantage since the components on the system undergo less stress than those systems needing higher amounts of energy. In those systems requiring higher energy, RF energy is often delivered in a pulsed fashion or for a specific duty cycle to prevent stressing the components of that system. In contrast, the reduced energy requirements of the present system allow for continual delivery of RF energy during a treatment cycle. In another variation, the duty cycle of variations of the present system can be pulsed so that temperature measurements can be taken between the pulsed deliveries of energy. Pulsing the energy delivery allows for an improved temperature measurement in the period between energy deliveries and provides precise control of energy delivery when the goal of the energy delivery is to reach a pre-determined temperature for a pre-determined time.

Figure 6:
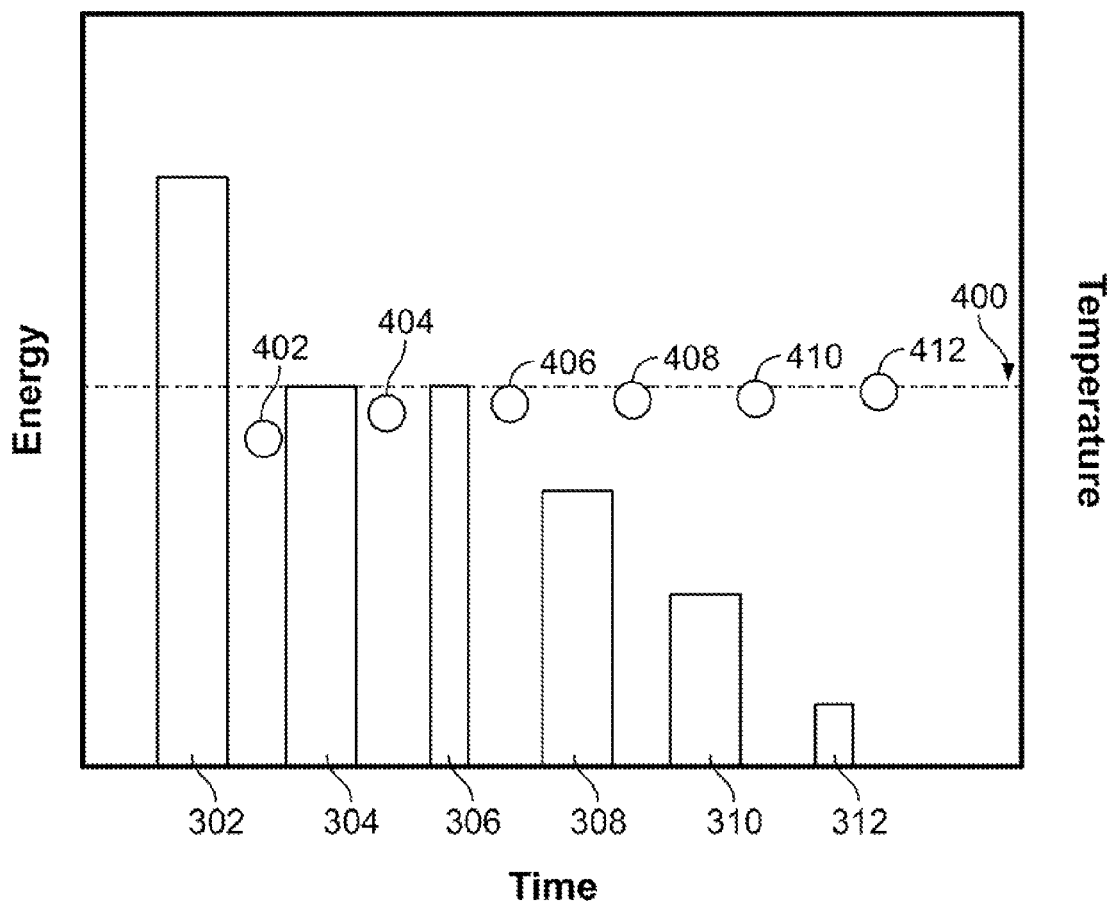
FIG. 6 illustrates a graph of energy delivery and temperature versus time.

FIG. 6 illustrates a graph of energy delivery and temperature versus time. As shown, the pulses or cycles of energy are represented by the bars 302, 304, 306, 308, 310, 312. Each pulse has a parameter, including amount of energy, duration, maximum energy delivered, energy wave form or profile (square wave, sinusoidal, triangular, etc), current, voltage, amplitude, frequency, etc. As shown in the graph, measurements are taken between pulses of energy. Accordingly, between each pulse of energy delivery one or more temperature sensor(s) near the probe obtains a temperature measurement 402, 404, 406, 408, 410, 412. The controller compares the measured temperature to a desired temperature (illustrated by 400). Based on the difference, the energy parameters are adjusted for the subsequent energy pulse. Measuring temperature between pulses of energy allows for a temperature measurement that is generally more accurate than measuring during the energy delivery pulse. Moreover, measuring between pulses allows for minimizing the amount of energy applied obtaining the desired temperature at the target region.

However, energy delivery control systems other than those described above can be employed. For example, in certain variations of the system, as described below, the probes measure parameters of the tissue. The system then applies energy to accommodate the parameters. For example, the probes can measure impedance of the surrounding tissue. The control system can then adjust an amount or a rate of energy depending upon the measured value.

As shown in FIG. 2B and as discussed above, the system 200 can extend a probe at an oblique angle relative to a tissue engagement surface 106. The ability to insert the probes into the tissue at an oblique angle increases the treatment area and allows for improved cooling at the tissue surface (directly above or in a direction normal to the probes). Although the variation only shows a single array of introducers for probes, variations of the invention may include multiple arrays of probes. The devices of the present invention may have an angle A of 20 degrees. However, the angle may be anywhere from ranging between 5 and 85 degrees (or as otherwise noted herein).

Figure 7A:
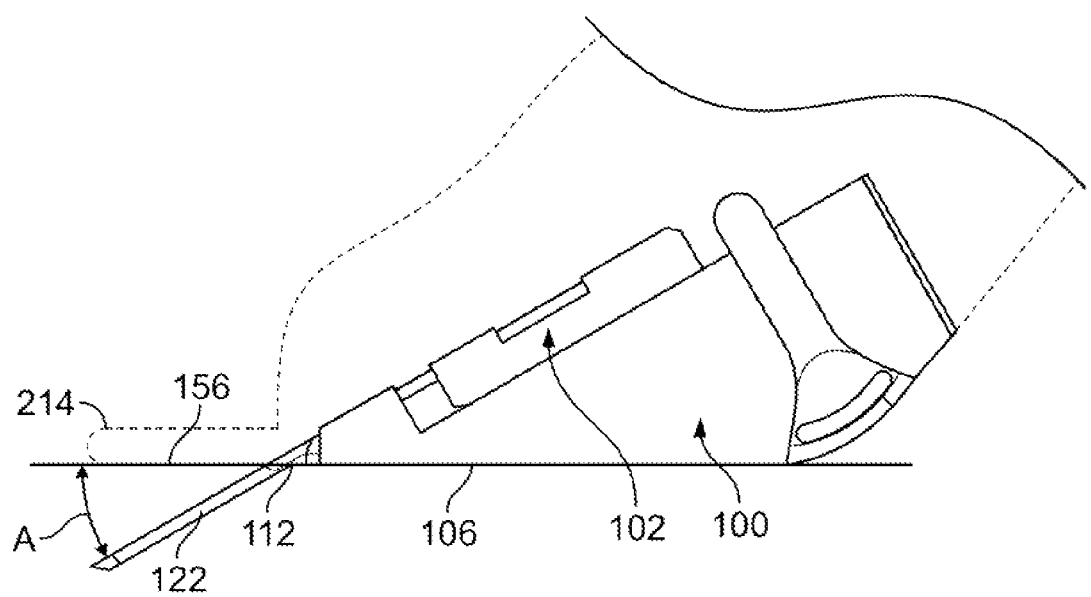
FIG. 7A illustrates a partial side view of probes entering tissue directly below a stabilization plate and oblique to a tissue engaging surface.

FIG. 7A illustrates a partial side view of the probes 104 and tissue engaging surface 106. For purposes of clarity, only the perimeter of the body portion 210 and stabilization plate 214 are shown. As shown, the probes 104 are advanceable from the device body 210 oil a cartridge 100 having a probe assembly 102. The probes enter tissue at an oblique angle A as measured relative to the tissue engagement surface 106 or stabilization plate 214. The tissue engagement surface 106 allows a user to place the device on the surface of tissue and advance the probes 104 to the desired depth of tissue. Because the tissue engagement surface 106 provides a consistent starting point for the probes, as the probes 104 advance from the device 202 they are driven to a uniform depth in the tissue.

For instance, without a tissue engagement surface, the probe 104 may be advanced too far or may not be advanced far enough such that they would partially extend out of the skin. As discussed above, either case presents undesirable outcomes when attempting to treat the dermis layer for cosmetic effects. In cases where the device is used for tumor ablation, inaccurate placement may result in insufficient treatment of the target area.

Figure 7B:
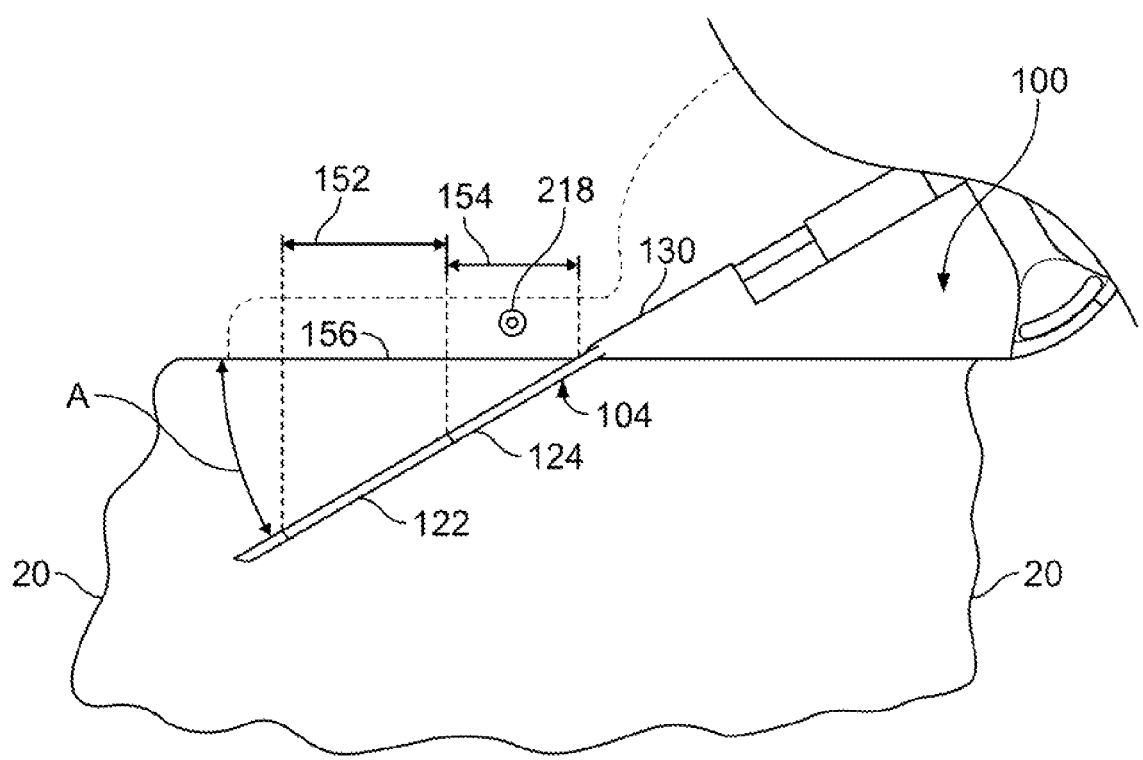
FIG. 7B illustrates a magnified view of the probes entering tissue at an oblique angle relative to the tissue engaging surface.

FIG. 7B illustrates a magnified view of the probes 104 entering tissue 20 at an oblique angle A with the tissue engaging surface 106 resting on the surface of the tissue 20. As is shown, the probe 104 can include an active area 122. Generally, the term "active area" refers to the part of the probe through which energy is transferred to or from the tissue. For example, the active area could be a conductive portion of a probe, it can be a resistively heated portion of the probe, or even comprise a window through which energy transmits to the tissue. Although this variation shows the active area 122 as extending over a portion of the probe, variations of the device include probes 104 having larger or smaller active areas 122.

In any case, because the probes 104 enter the tissue at an angle A, the resulting lateral region of treatment 152, corresponding to the active area 122 of the probe is larger than if the needle were driven perpendicular to the tissue surface. This configuration permits a larger treatment area with fewer probes 104. In addition, the margin for error of locating the active region 122 in the desired tissue region is greater since the length of the desired tissue region is greater at angle A than if the probe were deployed perpendicularly to the tissue.

As noted herein, the probes 104 may be inserted into the tissue in either a single motion where penetration of die tissue and advancement into the tissue are part of the same movement or act. However, variations include the use of a spring mechanism or impact mechanism to drive the probes 104 into the tissue. Driving the probes 104 with such a spring-force increases the momentum of the probes as they approach tissue and facilitates improved penetration into the tissue. As shown below, variations of the devices discussed herein may be fabricated to provide for a dual action to insert the probes. For example, the first action may comprise use of a spring or impact mechanism to initially drive the probes to simply penetrate the tissue. Use of the spring force or impact mechanism to drive the probes may overcome the initial resistance in puncturing the tissue. The next action would then be an advancement of the probes so that they reach their intended target site. The impact mechanism may be spring driven, fluid driven or via other means known by those skilled in the art. One possible configuration is to use an impact or spring mechanism to fully drive the probes to their intended depth.

Inserting the probe at angle A also allows for direct cooling of the surface tissue. As shown in FIGS. 7A and 7B, the area of tissue on the surface 156 that is directly adjacent or above the treated region 152 (i.e., the region treated by the active area 122 of the probe 104) is spaced from the entry point by a distance or gap 154. This gap 154 allows for direct cooling of the entire surface 156 adjacent to the treated region 152 without interference by the probe or the probe mounting structure. In contrast, if the probe were driven perpendicularly to the tissue surface, then cooling must occur at or around the perpendicular entry point.

As shown, the probe 104 enters at an oblique angle A such that the active region 122 of the probe 104 is directly adjacent or below the cooling surface (in this case the stabilization plate 214). In certain variations, the cooling surface 216 may extend to the entry point (or beyond) of the probe 104. However, it is desirable to have the cooling surface 214 over the probe's active region 122 because the heat generated by the active region 122 will have its greatest effect on the surface at the surface location 156. In some variations, devices and methods described herein may also incorporate a cooling source in the tissue engagement surface.

As discussed above, the cooling surface/stabilization plate 214 and cooling device coupled thereto can be any cooling mechanism known by those skilled in the art. For example, it may be a manifold type block having liquid or gas flowing through for convective cooling. Alternatively, the cooling surface 214 may be cooled by a thermoelectric cooling device (such as a fan or a Peltier-type cooling device). In such a case, the cooling may be driven by energy from the probe device thus eliminating the need for additional fluid supplies. One variation of a device includes a cooling surface 214 having a temperature detector 218 (thermocouple, RTD, optical measurement, or other such temperature measurement device) placed within the cooling surface. The device may have one or more temperature detectors 218 placed anywhere throughout the cooling surface 216 or even at the surface that contacts the tissue.

In one application, the cooling surface 214 is maintained at or near body temperature. Accordingly, as the energy transfer occurs causing the temperature of the surface 156 to increase, contact between the cooling surface 214 and the tissue 20 shall cause the cooling surface to increase in temperature as the interface reaches a temperature equilibrium. Accordingly, as the device's control system senses an increase in temperature of the cooling surface 214 additional cooling can be applied thereto via increased fluid flow or increased energy supplied to a Peltier-type device. The cooling surface can also pre-cool the skin and underlying epidermis prior to delivering the therapeutic treatment. Alternatively, or in combination, the cooling surface can cool the surface and underlying epidermis during and/or subsequent to the energy delivery where such cooling is intended to maintain the epidermis at a specific temperature below that of the treatment temperature. For example the epidermis can be kept at 30 degrees C. when the target tissue is raised to 65 degrees C.

When treating the skin, it is believed that the dermis should be heated to a predetermined temperature condition, at or about 65 degree C, without increasing the temperature of the epidermis beyond 42 degree C. Since the active area of the probe designed to remain beneath the epidermis, the present system applies energy to the dermis in a targeted, selective fashion, to dissociate and contract collagen tissue. By attempting to limit energy delivery to the dermis, the configuration of the present system also minimizes damage to the epidermis.

While the cooling surface may comprise any commonly known thermally conductive material, metal, or compound (e.g., copper, steel, aluminum, etc.). Variations of the devices described herein may incorporate a translucent or even transparent cooling surface. In such cases, the cooling device will be situated so that it does not obscure a view of the surface tissue above the region of treatment.

In one variation, the cooling surface can include a single crystal aluminum oxide ($Al_2O_3$). The benefit of the single crystal aluminum oxide is a high thermal conductivity optical clarity, ability to withstand a large temperature range, and the ability to fabricate the single crystal aluminum oxide into various shapes. A number of other optically transparent or translucent substances could be used as well (e.g., diamond, other crystals or glass).

Figure 7C:
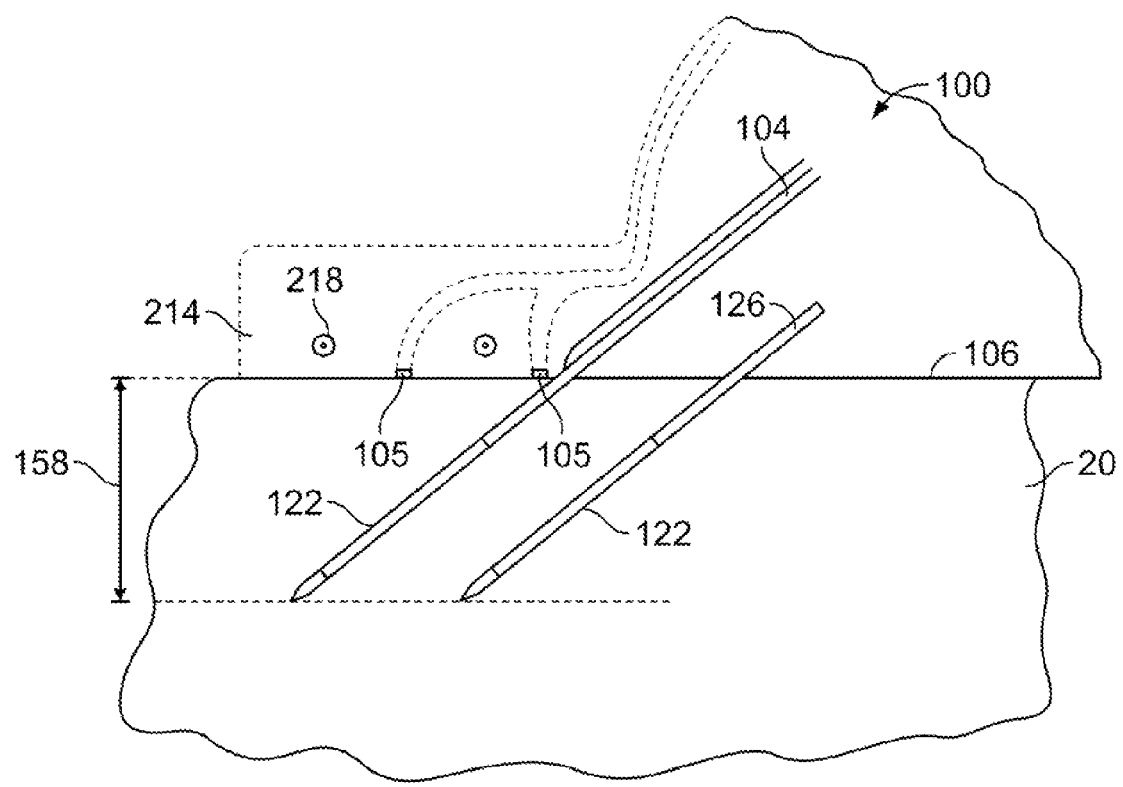
FIG. 7C illustrates additional variations of devices and methods described herein using temperature sensors and/or additional energy transfer elements in the stabilization plate.

FIG. 7C illustrates another aspect for use with variations of the devices and methods described herein. In this variation, the cartridge 100 includes two arrays of probes 104, 126. As shown, the first plurality 104 is spaced evenly apart from and parallel to the second plurality 126 of probes. In addition, as shown, the first set of probes 104 has a first length while the second set of probes 126 has a second length, where the length of each probe is chosen such that the sets of probes 104, 126 extend into the tissue 20 by the same vertical distance or length 158. Although only two arrays of probes are shown, variations of the invention include any number of arrays as required by the particular application. In some variations, the lengths of the probes 104, 126 are the same. However, the probes will be inserted or advanced by different amounts so that their active regions penetrate a uniform amount into the tissue. As shown, the cooling surface may include more than one temperature detecting element 218.

FIG. 7C also illustrates a cooling surface/stabilization plate 214 located above the active regions 122 of the probes. FIG. 7C also shows a variation of the device having additional energy transfer elements 105 located in the cooling surface 216. As noted above, these energy transfer elements can include sources of radiant energy that can be applied either prior to the cooling surface contacting the skin, during energy treatment or cooling, or after energy treatment.

Figure 7D:
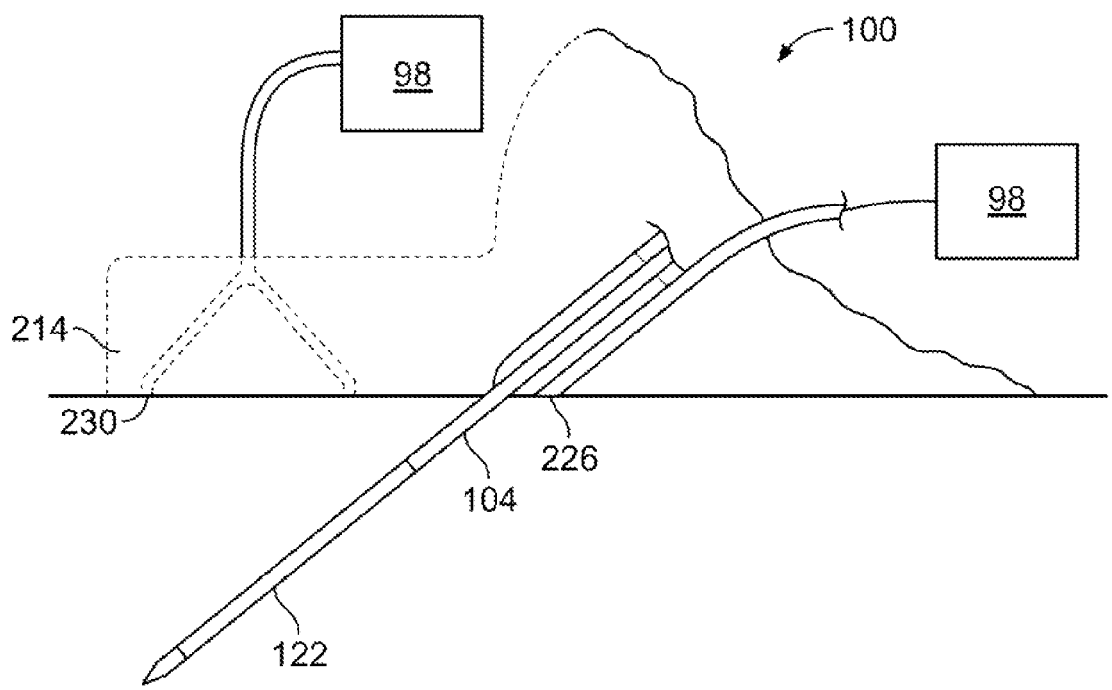
FIG. 7D shows the use of one or more marking lumens.

FIG. 7D shows an aspect for use with methods and devices of the invention that allows marking of the treatment site. As shown, the cartridge 100 may include one or more marking lumens 226, 230 that are coupled to a marking ink 98. During use, a medical practitioner may be unable to see areas once treated. The use of marking allows the practitioner to place a mark at the treatment location to avoid excessive treatments. As shown, a marking lumen 226 may be placed proximate to the probe 104. Alternatively, or in combination, marking may occur at or near the cooling surface 216 since the cooling surface is directly above the treated region of tissue. The marking lumens may be combined with or replaced by marking pads. Furthermore, any type of medically approved dye may be used to mark. Alternatively, the dye may comprise a substance that is visible under certain wavelengths of light. Naturally, such a feature permits marking and visualization by the practitioner given illumination by the proper light source but prevents the patient from seeing the dye subsequent to the treatment.

Figure 7E:
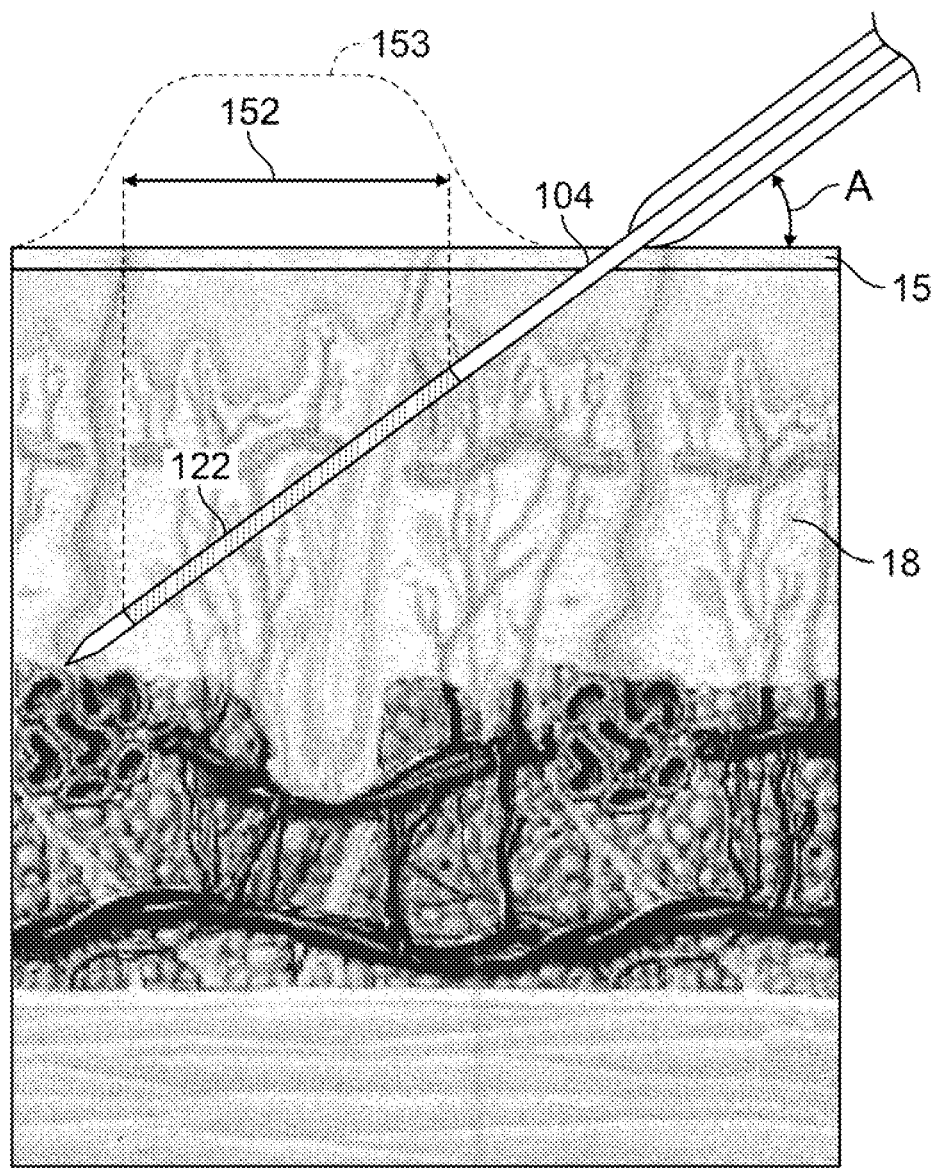
FIG. 7E shows another example of a probe entering tissue at an oblique angle underneath a skin anomaly.

FIG. 7E illustrates an example of the benefit of oblique entry when the device is used to treat the dermis 18. As shown, the length of the dermis 18 along the active region 122 is greater than a depth of the dermis 18. Accordingly, when trying to insert the probe in a perpendicular manner, the shorter depth provides less of a margin for error when trying to selectively treat the dermis region 18. As discussed herein, although the figure illustrates treatment of the dermis to tighten skin or reduce wrinkles, the device and methods may be used to affect skin anomalies 153 such as acne, warts, sebaceous glands, tattoos, or other structures or blemishes. In addition, the probe may be inserted to apply energy to a tumor, a hair follicle, a fat layer, adipose tissue, SMAS, a nerve or a pain fiber or a blood vessel. When treating such anomalies 153, the stabilization plate (not shown) can either include an opening to accommodate the anomaly 153 or can be made of a flexible material to conform to the anomaly 153.

Figure 8A:
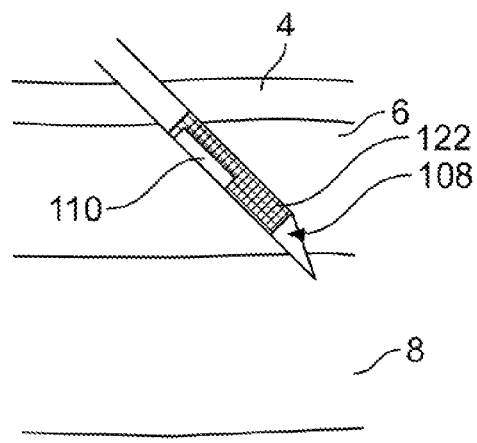
FIGS. 8A to 8C illustrates multiple sensors on electrodes/probes for measuring tissue parameters to adjust treatment parameters for improved therapeutic results or safety.

FIG. 8A illustrates another aspect for use with the systems and methods described herein. In this variation, the system is able to precisely deliver energy to target tissue for optimal therapeutic results. More specifically, this feature allows automated target tissue parameter measurement and uses that measurement to automatically enable and control energy delivered to the target tissue to optimize the desired effect of the energy on the tissue.

As shown, insertion of a probe 108 into tissue 20 creates a direct contact with target tissue that is below a surface 22 of the tissue 20. Because of this direct contact, the probe 108 can measure several tissue properties or parameters. For example, such properties include, but are not limited to: electrical impedance, the phase angle of the electrical impedance, acoustic impedance, hydration, moisture content, electromagnetic reflectance/absorption, temperature, movement, and elasticity. Measurement of these parameters provides specific information such as the type of tissue, tissue health, tissue depth or location of sensing/treatment cannula relative to tissue surface or relative to target and non-target tissues, potential response of tissue to subsequent treatment, or actual response of tissue to the present or previous treatments.

Referring to FIG. 8A, showing a partial section of a probe 108 placed in tissue 20 Note that while a single probe is illustrated, the features described herein are applicable to the array of probes and devices as discussed above. In this example, the target tissue is shown as a third layer 8. However, to reach the targeted tissue (the third layer 8), the probe 108 must cross two different layers or types of tissue 4, 6. The probe 8 contains a sensor 110 near a distal end or on an active area 122 of the probe 108. Alternatively, the entire active area 122 of the probe can function as a sensor.

Figure 8B:
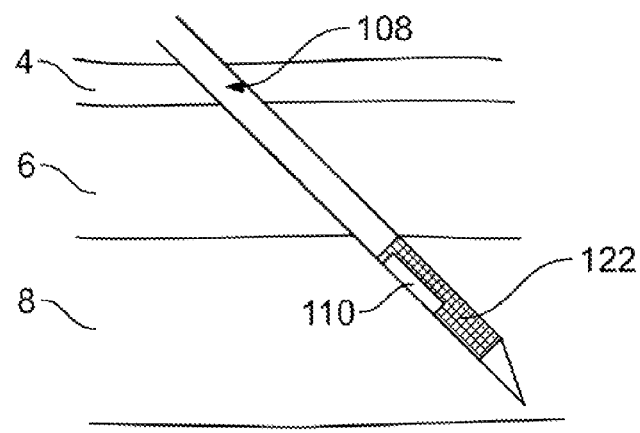

Measurement of a tissue parameter by the sensor 110 provides information that can confirm whether the probe 108 is located in the desired target region. For example, when measuring impedance of the tissue, if the measured impedance is not within a range normally associated with tissue, the system can prevent treatment and alert the user for the need to reposition the probe 108. Accordingly, the probe 108 can ultimately be repositioned as shown in FIG. 8B (or the active area 122 of the probe 108 can be repositioned).

In one variation, the probe 108 can employ an RF energy mode to denature or coagulate collagen in a dermal layer. In such a case, the probe 108 can be used separately from the active region 122, or the active region 122 can function as a sensor. In either case, the probe applies a very low level of current to the tissue to measure the tissue's impedance. The epidermis tissue layer comprises a very high impedance. The papillary epidermis layer has relatively low impedance (150-250 Ohms). The reticular dermis layer has impedance in the range of 250 to 2000 Ohms. Below the dermis lies a subcutaneous adipose layer that has high impedance (2500 to 5000 Ohms). By measurement of the impedance adjacent to the sensor or active region 122 the positioning depth of the probe 108 can be confirmed or determined and treatment can be applied to the targeted tissue 8.

When using a probe array, tissue adjacent to each probe can measure and energy can be applied only to those probes that are properly placed. Additionally, certain tissue structures including vessels and sebaceous glands within the dermal layer may be identified by the properties discussed herein. Probes in an array that are spaced sufficiently close will measure the impedance of the immediate structure rather than the surrounding dermal tissue. This information can be provided to the user for placement adjustment, or used to directly to prevent or adjust treatment for that cannula electrode pair.

In an alternative variation, the probe can employ light at two wave lengths 650 nm and 805 nm from a light source into the adjacent tissue. The light is partially absorbed and partially reflected based on the amount of hemoglobin in red blood cells in the adjacent tissue. The reflected light is captured by a fiber optics placed in or near the probe and directed to a detector which provides a reading to the energy controller. This reading can be used to stop energy delivery when the red blood cells in the adjacent tissue have been coagulated (the desired treatment end point) and as a result the light reflection reading has changed.

Figure 8C:
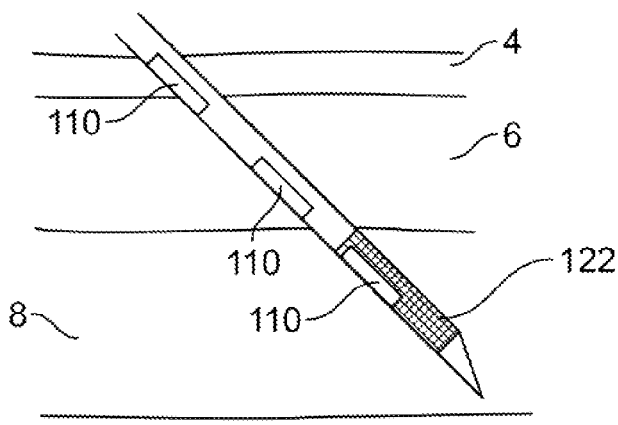

FIG. 8C illustrates another variation of a probe configuration. In this example, the probe 108 comprises several sensors 110. The probe 108 is shown crossing varying layers or types of tissue 4, 6, and 8. The spaced sensors 110 permit the user to verify that the active region 122 of the probe 108, is located substantially in the target tissue (in this example, region 8 and the other portion of the probe 108 are located substantially in non-target tissues layers 4 and 6.

The measured tissue parameters do not have to be provided to the user for the user to make adjustments to the tissue treatment. The parameters maybe used to automatically adjust treatment in any manner of ways with the use as part of the invention of a controller to read the parameters and adjust treatment.

In one variation, an RF delivery device having ten probe-electrodes was configured to deliver energy via 5 independent and electrically isolated probe-electrode pairs. The device was coupled to a controller comprising a bi-polar RF generator having 5 independent channels. The configuration of the electrodes was as described above (e.g., oblique insertion, cooling at a tissue surface, etc). Once the electrodes were placed in the tissue, a small level of current was independently delivered to each of the 5 bi-polar pairs to measure the impedance between each of the electrodes in the pair. When the impedance of a pair was within a predetermined level the controller directed delivery of RF treatment current to that pair. The advantage of using independent and electrically isolated channels each associated with only one electrode pair was to be able to create independent lesions and better adapt the energy delivery to the local conditions of the tissue. Simultaneously or sequentially if the impedance of any electrode pair is not within a specific range, then the controller prevents delivery of RF current to that pair. Additional variations of this configuration can employ any number of paired probes.

The system can further incorporate a variety of control algorithms to control the power applied to the treated tissue based on any number of criteria. In one variation, it was found that maintaining the temperature at a pre-determined value and monitoring impedance of tissue resulted in a significant increased treatment effect while minimizing collateral damage to tissue.

In one variation, the system monitors the initial impedance of the tissue and uses an algorithm including a PID (Proportional, Integral, Derivative) control which controls the input voltage between a pair of electrode. The control voltage (V) is given by the following equation:

$$V = k_p \cdot (T_{set} - T_{measured}) + k_I \cdot \int (T_{set} - T_{measured}) dt + k_d \cdot \frac{\partial (T_{set} - T_{measured})}{\partial t}$$

where $k_p$, $k_i$, and $k_d$ are constants, $T_{set}$ is the set point temperature, and $T_{measured}$ is the measured temperature. This control system first compares the actual electrode temperature $T_{measured}$ (or temperature of the damaged tissue) to the set point temperature $T_{set}$. If the two temperatures are very far apart then the system delivers a proportionally higher voltage. If temperatures relatively close, then the system gradually increases the voltage. The proportional increase in voltage is based on the $k_p$ coefficient that applies to the proportional aspect in the PID equation (tile first tend in the above equation). The PID also monitors the "rate of change" (derivative) between the measured temperature $T_{measured}$ and the set point temperature $T_{set}$. A change to the $k_d$ coefficient impacts the rate at which the system increases voltage. In other words, a voltage is applied, a temperature is measured, and the system increases the voltage to try to get the temperature up to the set point. This relates to the third term in the above equation. Usually, a relatively small $k_d$ coefficient is used in order to make sure that control variable, V in this case, is not too sensitive to the noise. The same logic applies to the integral (change in area "under the curve") coefficient.

The system constantly monitor the difference between the set and measured temperature and adjusts the input voltage accordingly until a steady state is achieved. At the steady state condition, there is no difference between the set and measured temperature. As a consequence, the only non-zero term of the above equation is the integral part (the third term). In such a condition, the input voltage V is kept the constant, which keeps the measure temperature $T_{measured}$ equal to the set temperature $T_{set}$. If something changes in the overall system, the controller will detect a variation in temperature difference and readjust the input voltage to bring the measured temperature back to the set point.

Figure 11A:
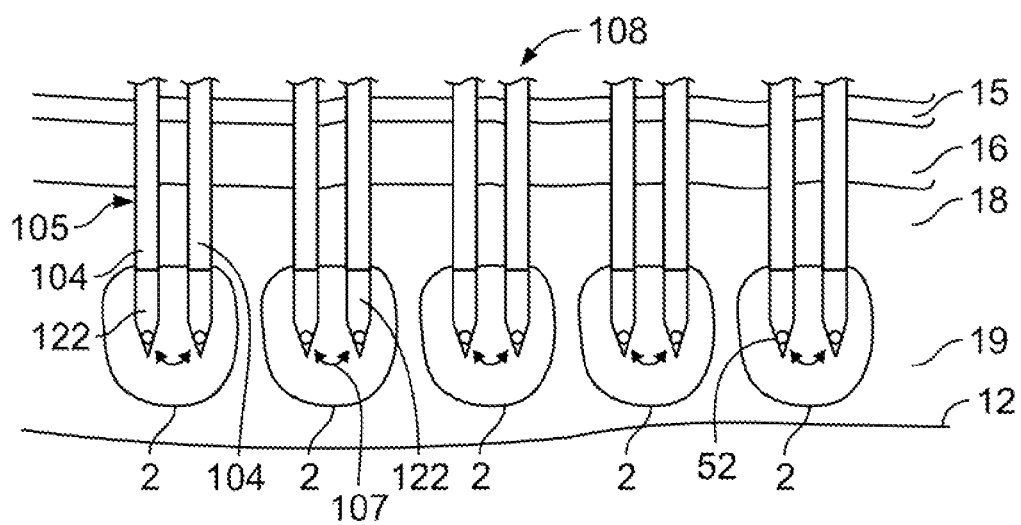
FIG. 11A shows an example of a series of discrete focal lesions created in a reticular dermis.

It should be appreciated that, in one variation, an independent PID controller, along with at least one independent temperature sensor, would be associated with only one pair of electrodes, which is electrically isolated from the other pair(s) of electrodes. Therefore, applying a current an electrically isolated pair of electrodes creates a fractional lesion confined within the exposed pair of the electrode (as shown in FIG. 11A). In other words, since all channels are electrically isolated, the current passing between each electrode of an electrically isolated pair will not be coupled to another electrode of another electrically isolated pair. Controlling the current flow in this manner allows for creation of a lesion along the entire length of the active area of the electrode and confined between electrodes of the pair. This treatment can also limit the lesion to the whole layer of tissue, or a substantial part of the tissue layer such as, for example, the dermal layer. Creation of lesion confined to a layer is typically not possible when only the distal end of the probe is the source of current flow.

In the above variation, the initial energy applied to the electrode pair in each pair in the array is under a very low voltage and with a low current. This allows measurement of the initial impedance. If the initial impedance is low (e.g., 250-700 ohms) the system applies a first set of PID coefficients. If the system measures moderate impedance, the system applies a second set of PID coefficients. It the system measures a high impedance the system applies a third set of coefficients to get the temperature up to the set point quickly, without overshooting and without significant oscillation. Using a varying set of PID coefficients based on the impedance of the tissue also allows greater control of energy delivery and allows treatment of the desired tissue without excessive collateral damage. Accordingly, a series of discrete focal lesion, series of lesions, or a planar lesion in the desired tissue as further illustrated below. The values of the PID coefficients can be varied depending upon the type of tissue targeted. In one example, the coefficients were as follows: Band 1: 250-700 Ohms, $k_p=29$, $k_I=41$, $k_d=0$, (with voltage limited to a maximum of 100 V); Band 2: 701-1500 Ohms, $k_p=43$, $k_I=70$, $k_d=10$, (with voltage limited to a maximum of 120 V); Band 3: 1501-3000 Ohms, $k_p=55$, $k_I=70$, $k_d=18$, (with voltage limited to a maximum of 120 V). The maximum voltages are set to avoid excessive power deposition in the targeted tissue. In addition, an adaptive PID system could be used to constantly optimize the PID coefficients ($k_p$, $k_I$ and $k_d$) based on the tissue response. Other adaptive systems commonly used in process control could also be used in this application.

In addition to the above, measuring properties of tissues can allow optimization of the treatment delivery itself. For example during RF delivery, high impedance tissue may be more optimally heated using higher voltages than may be safe there but inappropriate for lover impedance tissue since power deposited in tissue would be higher. Indeed, the power P deposited in the tissue is equal to the square of the voltage V divided by the impedance R as shown by the following equation:

$$P = \frac{V^2}{R}$$

In a multi-channel RF device, the tissue parameters measured for each cannula-electrode pair can be used to independently optimize the treatment parameters and algorithm for each channel. In those variations where all channels are electrically isolated and controlled independently with PID controllers the system would be capable of producing totally independent lesions in parallel where the PID controllers would be used to independently adjust the energy delivery in order to reach a target temperature. Since the local conditions of the skin could be different from one electrode pair to the other, it would be beneficial to drive all pairs independently in order to optimize the energy delivery necessary to reach a target temperature for each pair. Indeed, physical parameters associated with the lesion creation such as the electrical conductivity, the thermal conductivity, the heat capacitance, the perfusion rate, or the tissue density could be different from one location of the skin to the other. As a consequence, if all pairs were controlled in the same fashion, the thermal profile created in the skin, and therefore the associated created lesions could be very different from one pair to the other. Having electrically isolated pairs controlled with independent PID controller will therefore create more uniform and predictable lesions. Since the PID controllers are capable of optimizing energy delivery regardless of the skin condition, the lesions created are relatively independent of the skin condition and therefore more predictable and reliable. This aspect of the invention is quite beneficial to increase the efficacy and decrease the risk of the associated treatment.

Tissue parameter sensing is not limited to measuring between specific pairs of cannula. When more than 2 access cannula have been placed in the tissue, sensing can be done between any two cannulae to determine the tissue properties between those cannula.

Furthermore, the sensing of tissue parameters is not limited to only sensing prior to treatment delivery. Tissue parameters can be monitored during treatment to detect changes and adjust treatment according to those changes.

In addition to optimizing the treatment, the parameter measurement and automated treatment adjustment can also be utilized to improve patient tolerance or comfort of the treatment. For example, measurement of the parameter can be used to track the rate of change of the parameter and control energy delivery to maintain the rate of change to a tolerable level. If the parameter is temperature and it is know that an increase in temperature of 1 degree centigrade per second is tolerated by the patient's nervous system and an increase of 3 degrees centigrade is not well tolerated, the measured temperature can be used to deliver energy in a manner that limits temperature rise to approximately 1 degree per second.

Alternately two separate parameters can be measured to provide control for two different delivered energies. In this way a first temperature sensor in the body of the access cannula can be used to control delivery of a coolant (or current to a thermoelectric cooler) to the interior of the cannula to improve patient tolerance as a second temperature sensor that extends from the side or tip of the cannula is used to control delivery of energy to the target tissue such that the target tissue reaches a desired temperature which is higher than the cooled cannula temperature.

In another alternative the measured parameter is used to control the delivery of a material rather than energy. For example, the delivery of an ionic solution such as saline can be controlled to optimize the location and spread of the saline for conducting delivered electromagnetic energy. In another embodiment, the delivery of saline is controlled as a means of cooling the adjacent non-targeted tissue based on a measured parameter of a non-targeted tissue.

Figure 9A:
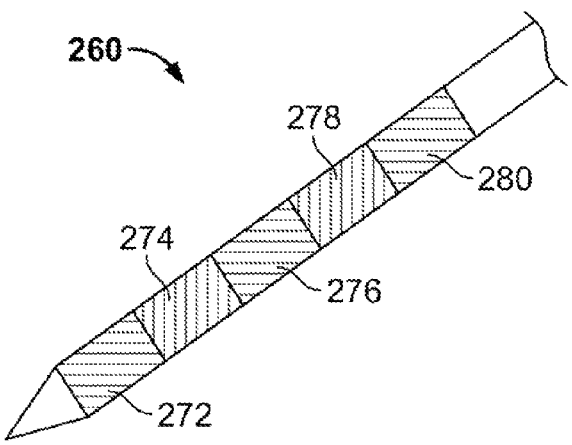
FIGS. 9A-9D illustrate variations of electrodes having varying resistance or impedance along the length of the electrode.
Figure 9B:
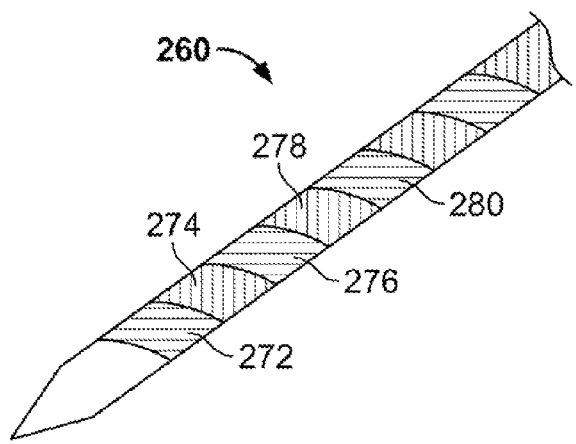
Figure 9C:
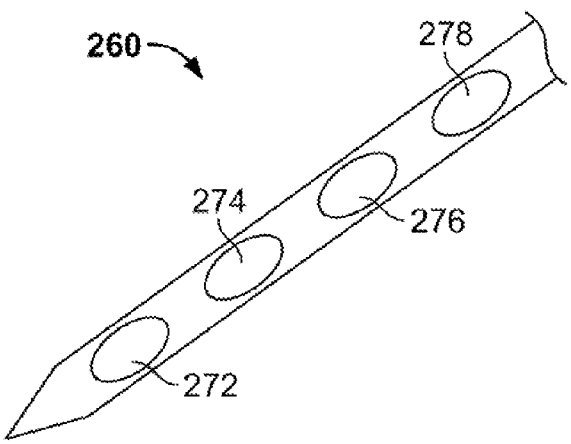
Figure 9D:
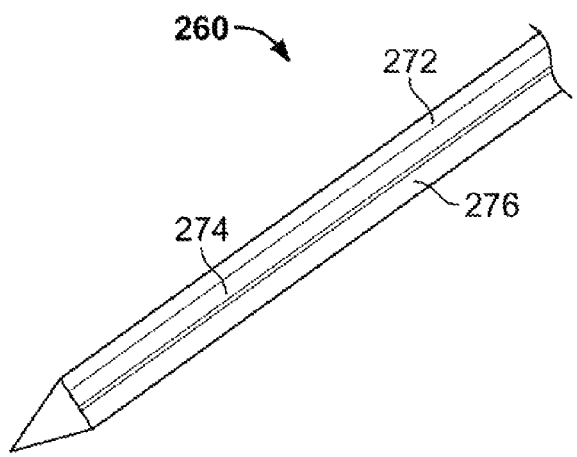

FIGS. 9A-9D illustrate variations of electrodes for use with the systems and methods described herein. Depending upon the application, it may be desirable to provide an electrode 260 that has a variable resistance along the active region of the electrode 260. FIGS. 9A-9D illustrate a partial example of such electrodes. As shown in FIGS. 9A and 9B, an electrode may have concentric or spiral bands that create varying ranges of impedance 272, 274, 276, 278, and 280 along the electrode 260. In addition, as shown in FIG. 9C, the electrode 260 may have regions 272, 274, and 276 and 278 along the electrode of varying resistance. FIG. 9D illustrates a similar concept where the regions of resistance 272, 274, and 276, run in longitudinal stripes along the electrode 260. These configurations may be fabricated through spraying, dipping, plating, anodizing, plasma treating, electro-discharge, chemical applications, etching, etc.

In any of the above variation, the energy sources can be configured as directional energy sources via the use of the appropriate insulation to direct energy to produce the treatment zones as described above.

Figure 10A:
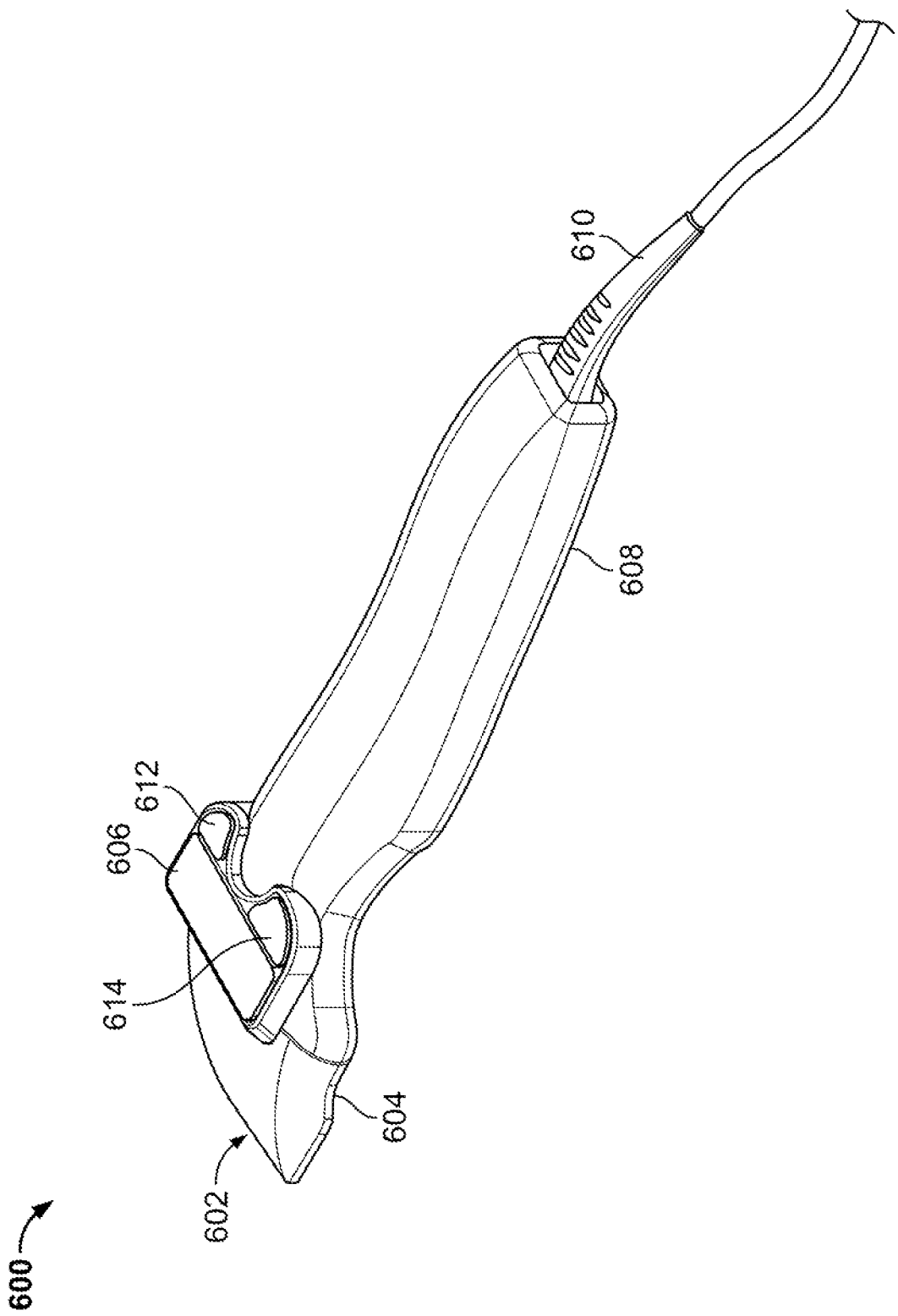
FIG. 10A is a perspective view of a variation of a device having an informational display located on a body unit of the system.
Figure 10B:
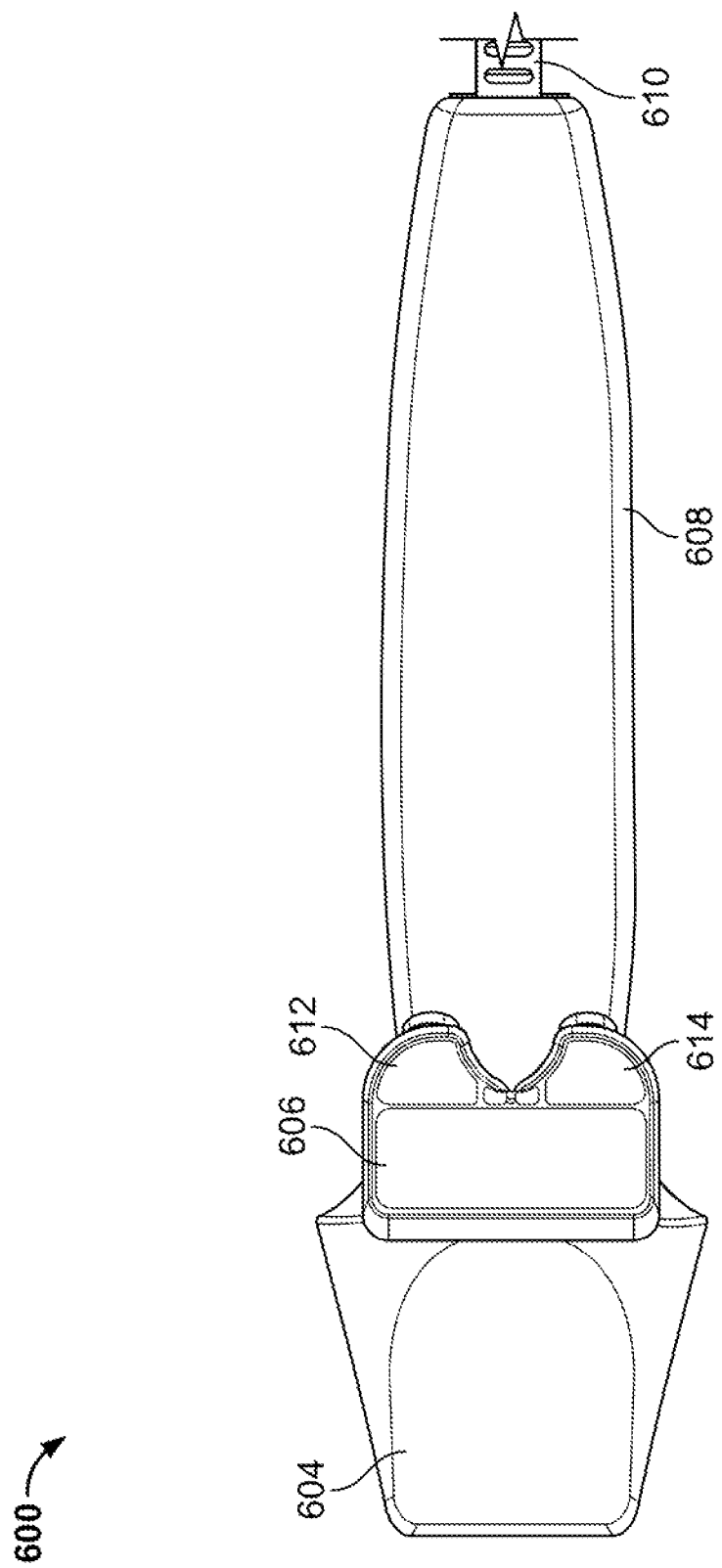
FIG. 10B is a top view of the device shown in FIG. 10A.

FIGS. 10A and 10B show an alternate variation of a device 600 comprising a handle 608 a detachable cartridge 604 on a distal end 602 and an electrical lead 610 on the proximal end. Also shown are a display screen 606 and actuators 612 and 614. The display screen 606 can display a variety of information to the physician such that the physician does not need to look at the energy supply means (not shown) for the information. Information such as treatment delivery settings, electrode impedance, electrode temperature, tissue temperature, treatment duration, power delivered, energy delivered, etc. can be displayed on the display screen 606 to facilitate effective and efficient treatment. The physician can use the information to make decisions and then adjustments by using the actuators 612 and 614 without the need to turn to the energy supply means to get the information or make the adjustments.

Although the systems described herein may be used by themselves, the invention includes the methods and devices described above in combination with substances such as moisturizers, ointments etc. that increase the resistivity of the epidermis. Accordingly, prior to the treatment, the medical practitioner can prepare the patient by increasing the resistivity of the epidermis. During the treatment, because of the increased resistivity of the epidermis, energy would tend to flow in the dermis.

In addition, such substances can be combined with various other energy delivery modalities to provide enhanced collagen production in the targeted tissue or other affects as described herein.

In one example, 5-aminolevulinic acid (ALA) or other photolabile compounds that generate a biologically active agent when present in the skin upon exposure to sunlight or other applied spectrums of activating light. Coatings or ointments can also be applied to the skin surface in order to stabilize the soft tissue. Temporarily firming or stabilizing the skin surface will reduce skin compliance and facilitate the insertions of the probes of the current device. An agent such as cyanoacrylate, spirit gum, latex, a facial mask or other substance that cures into a rigid or semi-rigid layer can be used to temporarily stabilize the skin. The topical ointments or coatings can be applied to enhance collagen production or to stabilize the skin for ease of probe insertion or both. Furthermore, topical agents can be applied to alter the electrical properties of the skin. Applying an agent which increases the impedance of the epidermal layer will reduce the conductance of RF current through that layer and enhance the conductance in the preferred dermal layer. A topical agent that penetrates the epidermal layer and is absorbed by the dermal layer can be applied that lowers the impedance of the dermal layer, again to enhance the conduction of RF current in the dermal layer. A topical agent that combines both of these properties to affect both the dermal and epidermal layers conductance can also be used in combination with RF energy delivery.

In addition to topical agents, the invention with its use of penetrating devices lends itself to the delivery of agents and materials directly to a specific region of tissue. For example, anesthetic agents such as lidocaine can be delivered through the probe to the dermis and epidermis to deaden nerve endings prior to the delivery of therapeutic energy. Collagen or other filler material can be delivered prior to, during or after energy delivery. Botulinum Toxin Type A, Botox, or a similar neurotoxin can be delivered below the skin layer to create temporary paralysis of the facial muscles after energy delivery. This maybe provide a significant improvement in the treatment results as the muscles would not create creases or wrinkles in the skin while the thermally treated collagen structure remodeled and collagenesis occurs.

Another means to enhance the tissue's therapeutic response is the use of mechanical energy through massage. Such an application of mechanical energy can be combined with the methods and systems described herein. Previously, devices have used massaging techniques to treat adipose tissue. For example, U.S. Pat. No. 5,961,475 discloses a massaging device that applies negative pressure as well as massage to the skin. Massage both increases blood circulation to the tissue and breaks done connections between the adipose and surrounding tissue. For example, these effects combined with energy treatment of the tissue to enhance the removal of fat cells.

EXAMPLE

Treatment Limited to a Reticular Dermis Layer

Patients were treated with a PID controlled bipolar RF electrode device (a frequency of 460 kHz) configured with 5 pairs of 30 gauge electrodes. The distance between two electrodes of a pair was about 1.25 mm, and the distance between two adjacent electrodes of an adjacent pair was about 2.5 mm. To protect the epidermis from RF heating at the insertion location, a proximal 3 mm of each electrode was insulated with a low-conductivity biocompatible material such as Teflon while the distal 3 mm were left exposed to function as the active portion. The treatment device body featured a smart electrode deployment system as described above. In such a system, the electrodes were configured to enter the epidermis at a 20° angle to the skin surface for a distance of 6 mm. Once inserted, each electrode pair transmitted a test current therebetween to sense the impedance of the tissue adjacent to the active portion of the electrodes. The test current is insufficient to create a lesion. The impedance values were found to be a reliable indicator of electrode depth and were used to guide deployment technique. Each of the 5 electrode pairs were controlled independently by the generator.

When deployed correctly, the active portion of the electrodes were positioned at a vertical distance of 2 mm from the epidermal surface. Each electrode pair included a temperature sensor at the active portion (in this example at the distal tip) to provide real-time feedback of tissue temperature from within the forming lesion. This temperature feedback system allows lesion temperature, rather than power, to function as the control parameter and for accurate pre-selection of temperature. It further allows for maximal power utilization at the start of each treatment cycle in order to reduce the ramp time to reach target temperature and then reduced power as required to maintain this temperature for the preset treatment duration.

Impedance values for the reticular dermis were typically between 500 to 2000 ohms. During treatment, the measured impedance frequently varied both with lesion temperature and with time-at-temperature. The impedance of the superficial papillary dermis was typically less than 300 ohms while that of subcutaneous adipose tissue was typically more than 3500 ohms. The impedance of the stratum corneum, the most outer layer of the epidermis, is much higher than the papillary or reticular dermis. Therefore, the needles were positioned in the dermal layer which is embedded between two layers of high impedance (the stratum corneum and the subcutaneous layer). The current passing through the probe will preferentially take the path of least resistance. As noted herein, the controller applies the current in a manner that limits current flow through the dermal layers. As a consequence, the heating profile will be preferentially located in the dermal layer where the current is flowing. Obtaining a preferential energy deposition in the dermal layers is beneficial to promote new collagen and elastin, which is beneficial to treat wrinkles and skin laxity for example.

The impedance measurement system was used to detect the layer of skin in which the needles were deployed. This feature gave real-time information to the physician that was used to confirm proper needle deployment and needle depth information within the skin. Adjacent needle pairs frequently encountered different impedances although values still fell within the range typical for the reticular. During treatment, as the target temperature was approached, the system reduced the power during the maintenance phase, thereby minimizing temperature overshoot.

The temperature in the above example was adjusted from 60 to 80° C. and the time-at-temperature was adjusted from 1.5 to 25 seconds. During a later phase of the study, the treatment temperature was held at 70° C. using the system described above and the time-at-temperature was set to 1, 4, or 7 second(s). A higher temperature setting of 78° C. for 4 seconds was also used toward the end of the study with excellent clinical results and safety profile.

FIG. 11A shows an example illustration of an array of probes 108 comprising five electrode pairs 105 inserted into a reticular dermis layer 19 to create a series of discrete fractional lesions 2 leaving tissue in the adjacent epidermal layer 16 and subcutaneous layer 12 undamaged. Essentially, the zones of thermal coagulation are located in the reticular dermis 19 and are typically entirely surrounded by a spared zone of normal dermis. This is accomplished by passing current 107 between adjacent electrodes 104 of opposite polarity in the electrode pair.

Figure 11B:
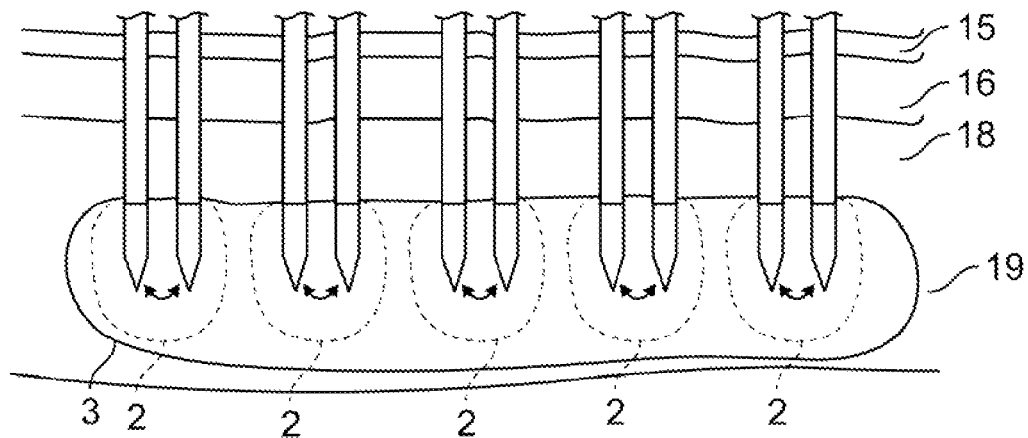
FIG. 11B shows the discrete focal lesions increasing in a width of the reticular dermis layer without damaging adjacent tissue.

As shown in FIG. 11B, when desired, the width of the fractional lesion 2 can be increased as the time-at-temperature is increased. As shown, the plurality of focal lesions 2 can combine to form a single lesion 3 without expanding to the adjacent layers. This effect is possible by adjusting pulse duration to merge the fractional lesions 2 into a contiguous planar lesion 3.

In some applications, it might be beneficial to create discrete small focal lesions as described in FIG. 11A as opposed to a larger and more uniform lesion described in FIG. 11B. In the field of cosmetic applications, this is commonly known as fractional technology which is thought, as described in U.S. publication no. US20080058783 (incorporated by reference herein), to be a safer method of treatment of skin for cosmetic purposes since tissue damage occurs within smaller sub-volumes or islets within the larger volume of tissue being treated. It has been shown that, since the tissue surrounding the islets is spared from the damage and remains viable, the healing process is more thorough and faster as compared to a larger continuous lesion. Furthermore, it is believed that the surrounding viable tissue aids in healing and the treatment effects of the damaged tissue. This viable tissue (either immediately after treatment or at some point subsequent to the treatment) can provide blood and/or cells, to assist in the healing process of the fractional lesion. In some cases, it may be desired to create the fractional lesions sequentially. For example, referring to FIG. 11A, a pair of probes can produce a fractional lesion while one or more adjacent (or even all) probe pairs remains un-energized. Once the first lesion is created, subsequent lesions can then be created.

The creation of small sub-volume islets are much less likely to create a zones of dense scar tissue that is often associated with larger treated volumes. When a large volume of tissue is treated, the body has a tendency to isolate and encapsulate the treated tissue. Such a process often includes a remodeling phase creating granulated tissue. The granulated tissue is then replaced by a large zone of dense scar tissue over a period of several weeks. In the treatment of rhytids or skin laxity, the presence of such a large zone of dense scar tissue might not be desirable for cosmetic reasons. Therefore, for the treatment of rhytid and skin laxity, it would be beneficial to use an energy application setting with would lead to the creation of discrete fractional lesions and avoid creating larger continuous lesions in order to keep the benefits of fractional applications. Especially when such lesions are created in the dermal layer or reticular dermis without causing the lesion to form in the epidermis. For example, in certain device configurations mentioned herein, discrete fractional lesions were obtained when target temperature between 60° C. and 80° C. and time at temperature between 0 and 6 seconds. Settings to cause discrete fractional lesions are not restricted to these disclosed settings, and settings outside of this range would also produce discrete focal lesions.

Another aspect of this invention consists of creating discrete fractional lesions, that are totally embedded within a tissue. Typically, in the case of rhytid and skin laxity treatment, the target tissue layer is the dermal layer, and in some cases the reticular dermal layer. Fractional technology has been disclosed in several patent applications such as U.S. publication no. US20080058783 incorporated by reference, and clinical literature such as "Ex vivo histological characterization of a novel ablative fractional resurfacing device" in Lasers in Surgery and Medicine, Volume 39 Issue 2, Pages 87-95. However, at this time, these fractional applications are performed with laser from the tissue surface, the epidermal layer of the skin in most of the case, which involved the ablative energy to flow through at least the tissue surface. As a consequence, the discrete focal lesions include the tissue surface and are not totally embedded in the tissue. The use of other ablative energy such as high intensity focused ultrasound (HIFU) or RF energy to create lesions in a tissue layer from the tissue surface has also been disclosed (see U.S. Pat. No. 6,277,116, which is incorporated by reference.). Conventional energy modalities create discrete lesions in a tissue require the ablative energy to flow through at least the tissue surface. This situation is not desirable since it could lead to tissue surface damage and unpredictable lesion formation. However, as noted herein, it is desirable, when producing fractional lesions, to provide an electrode arrangement where all treated zones are independently created in order to deliver the energy in a way that is optimized for the local characteristics of the tissue at the precise location of energy delivery (i.e., the electrode pair that creates the fractional lesion). In addition, creating lesions along a length or portion of an electrode pair is desirable since the treated zone is confined to a specific layer of the tissue (for example, such as the dermal layers of the skin). In contrast, many devices create the lesion at an end of the electrode and do not control the damage to a particular layer.

The methods and apparatus described herein allow creation of an array of independently created discrete focal lesions, or fractional lesions, which are wholly embedded in to the tissue where the ablative energy is not applied through the tissue surface. Some of the benefits associated with this aspect of the invention consist of being capable of producing fractional lesions safely and consistently within the dermal layer by delivering the ablative energy directly into the target tissue, while protecting adjacent structure such as the epidermis or the subcutaneous layer.

In addition, a fractional pattern could be performed in a single insertion of an array of retractable probes, as described in FIG. 11A. The insertion of the array of retractable probes could be repeated at another adjacent location to increase the size of the final fractional pattern. Another technique would be to obtain the same final fractional pattern with only one probe by producing every discrete focal lesion sequentially and independently.

Figure 11C:
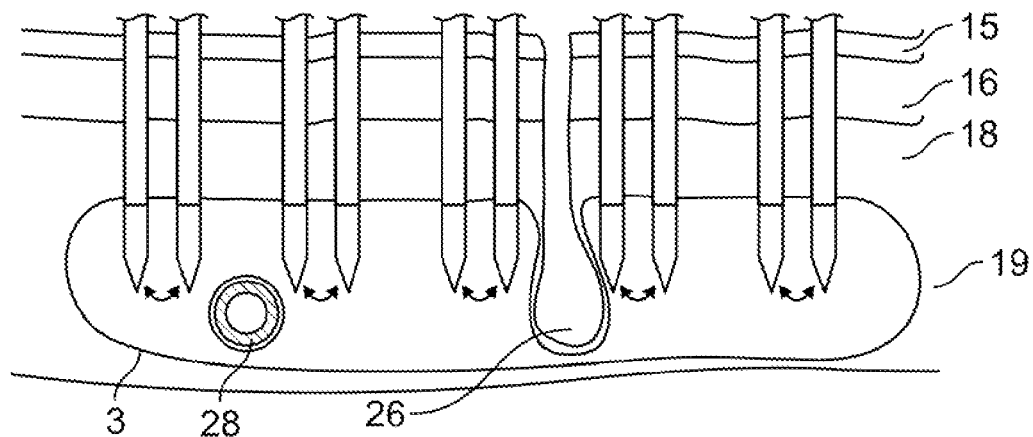
FIG. 11C shows an example of a lesion where the application of treatment via the electrode pairs avoids damage to adnexal structures in the reticular dermis.

In previous testing, treatment at the subcutis depth did not result in adipose ultra-structural changes or fat necrosis, although the device coagulated interstitial collagen. Treatments at the dermal 19 depth resulted in collagen coagulation as expected. However, due to the nature even though periadnexal collagen was coagulated, there was no evidence of coagulation of adnexal structures (such as blood vessel hair bulbs, sweat ducts, sebaceous glands, blood vessels, and other glands). Sparing of adnexal structures and adipose tissue was another unforeseen benefit provided by the systems and methods described herein. Since the electrodes are deployed within target tissue, current travels through the path of least resistance between electrode pairs. The lipid barriers surrounding adnexal structures and the high impedance of adipose tissue directs current and energy deposition through connective tissue and interstitial fluid. As shown in FIG. 11C, the resulting planar lesion 3 avoids hair follicles 26, blood vessels 28 as well as other adnexal structures in the reticular dermis 19.

The results of this study have shown that the variations of the present system can create radiofrequency thermal zones within the reticular dermis. It was demonstrated that lesion size can be controlled by varying treatment pulse duration and lesion temperature. Focal lesions surrounded by uninjured tissue were produced giving a true fractional response. With the added feature of using impedance measurements to precisely determine depth of placement of the active electrode portion 122, precision over depth control was made possible. This control over placement allowed tunable dosimetry permitting controlled delivery of a specific thermal coagulation profile at a particular depth in the dermis. Using these features ensured adequate sparing of normal tissue in all dimensions surrounding a focal lesion.

Based on previous laser-tissue interaction studies investigating the effects of fractional photothermolysis treatment with a 1550 nm fiber laser on the biological wound healing response, it is believe a that the present system can achieve similar rapid healing. In addition, the treatment as described herein demonstrates histological evidence of neocollagenesis and elastin replacement post-treatment as well as a rapid and vibrant heat shock protein response. In essence, the methods described herein provide for neocollagenesis and elastin production by creation of one or more focal lesions in the dermal layer.

Although the variations described herein primarily discuss the use of RF energy, other energy-based ablation modalities such as microwave, HIFU, laser, direct heat, or non-energy based such as injection of chemical agents could be used to create discrete fractional lesions.

For example, the fractional lesions discussed above can be created by inserting at least a pair of probes at least partially in a first layer of tissue, applying energy to the pair of probes in a controlled manner such that the energy damages tissue to create at least one fractional lesion adjacent to each probe and where each fractional lesion is surrounded by a layer of viable tissue. The mode of energy used can range from of electrical, electromagnetic, microwave, mechanical, ultrasound, light, radiation, chemical (the injector being at the focal point of the lesion 2 (e.g., at the tip of the probe 104), and radioactive energy. Moreover, a fractional lesion can be created using the bi-polar electrodes shown or a single monopolar electrode (so long as the lesion remains within an area of the electrode and does not grow to an adjacent electrode).

The methods of creating a fractional lesion can include creating the fractional lesion within a single layer of tissue and/or allowing the lesion to grow into a lesion 3 that comprises a number of joined fractional lesions that remain within a single layer of tissue (e.g., See FIG. 11B). As discussed herein, it may be desirable to spare adnexal and integral skin structures in the tissue. Therefore, setting selection, such as the target temperature and the time at temperature, can be selected to spare adnexal structure such as sweat gland, sebaceous gland, or hair follicle for example, or integral structural skin components such as elastin for example. It has been observed that sparing of adnexal structure was obtained with a temperature setting of about 70° C. with time at temperature within about 7 seconds. When time at temperature was increased to about 15 seconds, complete tissue ablation was observed with minimal or no sparing of adnexal structures. Histological evidence of post-treatment neocollagenesis and elastin replacement as well as rapid and vibrant heat shock protein response was also observed with the settings. These beneficial biological responses were mainly observed at a target temperature of about 70° C. with a time at temperature within about 7 seconds. From the overall experience with the device, the sparing of adnexal structure will be preserved at target temperature between about 65° C. to 75° C. with time at temperature of about 1 to about 10 seconds. It is also commonly accepted that the temperature threshold for elastin denaturation is above 100° C. Target temperature below this threshold would therefore be beneficial to preserve existing elastin. It should be understood that similar observation could be obtained with a system using a different control system. For example, the same observation could be made with a controller using a constant voltage, constant current, or with a feedback system using a measured parameter other than temperature. As an example, the other parameter could be impedance.

Through the use of real-time temperature feedback from within tissue during energy delivery allows the temperature to be pre-selected and subsequently be used to control delivery of energy. This ensured that appropriate clinical endpoints of peak temperature and time-at-temperature were reached but not exceeded during treatment applications.

Although variations of the system and methods described herein can employ any number of energy modalities. When used with a bi-polar RF energy modality, the use of minimally invasive micro-needle electrode pairs appears to have several clear advantages. Firstly, the system and methods allow for a very direct method to control the location within skin for energy delivery. The system and methods remove the uncertainty about chromophore location and removes the uncertainty of where energy is absorbed within the tissue. The system and method also allow tissue characteristics to be measured prior to delivery of treatment energy to both confirm treatment location and optimize the treatment algorithm in real-time.

Significant differences in the impedance of different tissue layers were observed. If the micro-electrodes were intentionally or inadvertently deployed subcutaneously into adipose tissue, the measured impedance was significantly higher than that of the reticular dermis. Similarly, if the electrodes were intentionally or inadvertently deployed superficially within the papillary dermis, impedances lower than those typical of the reticular dermis were observed. It was also noted by treating physicians that within the reticular dermis, higher impedances tended to correlate with deeper deployment. Within the reticular dermis, patient-to-patient and treatment location differences in the electrical and thermal characteristics of skin were observed. These differences highlighted the benefit of using lesion temperature and time-at-temperature as the control parameters rather than voltage, current, power or energy delivered.

A direct benefit of the minimally invasive approach is the ability to obtain real-time feedback of treatment effects through the use of temperature sensors strategically positioned at the distal end of the micro-electrode. Real-time temperature data permits uniformity in the tissue response.

Either fixed energy or fixed power control often results in significant variation in tissue response. This tissue response variability and lack of real-time feedback may be contributing factors to the complications and disappointing results seen with prior non-invasive devices.

Although this treatment is a minimally invasive procedure, local anesthesia was sufficient to prevent patient discomfort. Patients reported little to no discomfort either during or following treatment. Previous studies highlight the ongoing controversy surrounding the use of local anesthesia for laser procedures that employ water as a chromophore. Furthermore, manufacturers of non-invasive monopolar and bipolar RF devices recommend against infiltration with local anesthetic as it may alter energy deposition and heating patterns. On some occasions, infiltration of tissue with local anesthesia lowered tissue impedance compared to non-infiltrated sites. However, these impedance differences were detected by the present system through the temperature feedback described above. This allowed for correction in real-time leading to equivalent lesions throughout the treatment zone. The use of local anesthetic provides a significant advantage in pain management due to the restrictions on other non-invasive devices cited above.

The above variations are intended to demonstrate the various examples of embodiments of the methods and devices of the invention. It is understood that the embodiments described above may be combined or the aspects of the embodiments may be combined in the claims.

What is claimed is:

1. A method of cosmetically improving a tissue surface by applying energy to a region of tissue from an energy source, comprising:
   engaging a tissue engaging surface of an energy delivery device against the tissue surface, wherein the energy delivery service includes a hand-piece;
   engaging a tissue stabilization plate of the energy delivery device against the tissue surface, wheren in the tissue stabilization plate is adjacent to a side of the tissue engaging surface and extends past a side of the hand-piece, wherein the tissue stabilization plate and the tissue engaging surface are configured to hold the region of tissue flat and in line with the tissue engaging surface, wherein the region of tissue is between the tissue engaging surface and the tissue stabilization plate;
   tensioning and holding flat the region of tissue using the tissue stabilization plate and the tissue engaging surface;
   advancing a plurality of energy transfer probes of the energy delivery device from a retracted position to a treatment position inside the region of tissue,
   wherein the energy transfer probes extend from the energy delivery device at an oblique angle relative to the tissue engaging surface, wherein the tissue stabilization plate includes a window configured to permit direct visualization of insertion of the plurality of energy delivery probes into the region of tissue the step of advancing; and
   applying energy to the region of tissue at an active area of at least one of the plurality of energy transfer probes so as to cosmetically improve the tissue surface, wherein the tissue stabilization plate is configured to provide a visual frame of reference boundary outlining a perimeter of energy application.

2. The method of claim 1, where the plurality of energy transfer elements are comprised of a plurality of pairs of energy transfer probes and where applying energy to tissue at an active region of at least one of the plurality of energy transfer probes comprises first measuring an impedance of each pair of energy transfer probes; and applying energy to those pairs of energy transfer probes where the impedance between a range of pre-determined impedance values.

3. The method of claim 2, where the range of pre-determined impedance values comprises between 700 Ω to 3000 Ω.

4. The method of claim 3, where applying energy to the tissue further comprises applying energy to each pair of energy transfer probes using one of a plurality of predetermined energy delivery profiles, and selecting the predetermined energy delivery profile based upon the measured impedance.

5. The method of claim 4, where the energy delivery profile comprises a proportional-integral-derivative.

6. The method of claim 5, where the proportional-integral-derivative control further measures a temperature of tissue adjacent to the pair of energy delivery elements at different points in time during the energy application to control application of energy to cause the measured temperature to reach a pre-determined temperature.

7. The method of claim 1, where the plurality of energy transfer probes comprise a set of energy transfer probes and where the set of energy transfer probes are detachable from the energy transfer delivery device.

8. The method of claim 1, further comprising cooling the tissue stabilization plate.

9. The method of claim 1, further comprising providing a suction force at the tissue stabilization plate.

10. The method of claim 1, where advancing a plurality of energy transfer probes comprises advancing a plurality of arrays of energy transfer probes into tissue.

11. The method of claim 10, where the plurality of arrays of energy transfer probes are offset to prevent a continuous line of insertion points along the tissue.

12. The method of claim 10, where the plurality of arrays of energy transfer probes are energized at different times.

13. The method of claim 12, where the region of tissue comprises tissue selected from the dermis, a hair follicle, sebaceous gland, a skin anomaly such as acne, wart or other structure or blemish, and a blood vessel.

14. The method of claim 1, where the plurality of energy transfer probes are comprised of fiber optics and where applying energy to tissue at an active region of at least one of the plurality of fiber optics comprises directing laser energy through the at least one fiber optic.

15. The method of claim 1, where the plurality of energy transfer probes are comprised of a plurality of ultrasonic transducers and where applying energy to tissue at an active region of at least one of the plurality of transducers comprises energizing the at least one transducer.

16. The method of claim 1, where the plurality of energy transfer probes are comprised of a plurality of thermally resistive probes and where applying energy to tissue at an active region of at least one of the plurality of thermally resistive probes comprises supplying electrical current to the at least one probe.

17. The method of claim 1, where the plurality of energy transfer probes are comprised of a plurality of microwave antennae and where applying energy to tissue at an active region of at least one of the plurality of antenna comprises supplying microwave energy to the at least one antenna.

* * * * *